United States Patent [19]

Conover et al.

[11] Patent Number: 4,713,165
[45] Date of Patent: Dec. 15, 1987

[54] SENSOR HAVING ION-SELECTIVE ELECTRODES

[75] Inventors: Gilbert Conover, Providence, R.I.; Thaddeus Minior, Lawrence; John P. Willis, Harvard, both of Mass.

[73] Assignee: Ilex Corporation, Boston, Mass.

[21] Appl. No.: 881,099

[22] Filed: Jul. 2, 1986

[51] Int. Cl.⁴ ............................................. G01N 27/30
[52] U.S. Cl. .................................... 204/403; 204/411; 204/412; 204/416; 204/418; 422/68; 435/291; 435/817
[58] Field of Search ............... 204/403, 411, 412, 416, 204/418, 1 E; 435/817, 291; 422/68

[56] References Cited

U.S. PATENT DOCUMENTS

| | | | |
|---|---|---|---|
| 3,189,662 | 6/1965 | Vaughn | 260/824 |
| 3,429,785 | 2/1969 | Ross | 204/1 T |
| 3,438,886 | 4/1969 | Ross | 204/296 X |
| 3,445,365 | 5/1969 | Ross | 204/296 X |
| 3,539,455 | 11/1970 | Clark | 204/1 T |
| 3,691,047 | 9/1972 | Ross et al. | 204/296 X |
| 3,707,455 | 12/1972 | Derr et al. | 204/1 T X |
| 3,743,588 | 7/1973 | Brown, Jr. et al. | 204/195 M |
| 4,053,381 | 10/1977 | Hamblen et al. | 204/416 |
| 4,184,936 | 1/1980 | Paul et al. | 204/195 R |
| 4,214,968 | 7/1980 | Battaglia et al. | 204/195 M |
| 4,257,862 | 3/1981 | Schnipelsky et al. | 204/195 R |
| 4,353,867 | 10/1982 | Luzzana | 422/68 |
| 4,413,407 | 11/1983 | Columbus | 29/825 |
| 4,437,970 | 3/1984 | Kitajima et al. | 204/412 |
| 4,510,035 | 4/1985 | Seshimoto | 204/411 |

FOREIGN PATENT DOCUMENTS

| | | | |
|---|---|---|---|
| 0012035 | 6/1980 | European Pat. Off. | 204/411 |
| 0021798 | 1/1981 | European Pat. Off. | 204/416 |
| 0074198 | 3/1983 | European Pat. Off. | |

OTHER PUBLICATIONS

Ammann, et al., *Analytical Chemistry*, 53, No. 14, 2267-2269, Dec. 1981.
LeBlanc et al., *Journal of Applied Physiology*, 40: 644-647, (1976).
Vaugh, *Polymer Letters*, 7: 569-572, (1969).
Finkelstein, *Biochim. Biophys. Acta*, 205: 1-6, (1970).
M. Y. Keating et al., *Anal. Chem.*, 56, pp. 801-806, (1984).
Naoto Yamamoto et al., *Clin. Chem.*, 26/11, pp. 1569-1572, (1980).
Tekum Fonong et al., *Anal. Chem.*, 56, pp. 2586-2590, (1984).
Masuo Aizawa et al., *Analytica Chimica Acta*, 115, pp. 61-67, (1980).
Jean-Louis Boitieux et al., *Clin. Chem.*, 25, 318, (1979).
J. L. Boitieux et al., *Clin. Chemica Acta*, 113, pp. 175-182, (1981).
Hans Nilsson et al., *Biochimica Et Biophysica Acta*, 320, pp. 529-534, (1973).
Andrea Mosca et al., *Analytical Biochemistry*, 112, pp. 287-294, (1981).
M. Luzzana et al., *Clin. Chem.*, 29/1, pp. 80-85, (1983).
F. Ceriotti et al., *Clin. Chem.*, 31/2, pp. 257-260, (1985).

*Primary Examiner*—G. L. Kaplan
*Attorney, Agent, or Firm*—Hamilton, Brook, Smith & Reynolds

[57] ABSTRACT

A sensor and a method are disclosed for the potentiometric determination of the ion content or activity of a sample and the concentration of other components (e.g., glucose, urea, triglycerides, enzymes, drugs) of a sample. The sensor comprises ion-selective electrodes which are held in a frame and have porous material between them; the porous material provides a means to establish ionic flow between the electrodes. Each ion-selective electrode is comprised of a membrane which is selectively permeable to the ion or other substance whose activity or concentration is being determined; a reference electrode; and an internal reference material.

14 Claims, 21 Drawing Figures

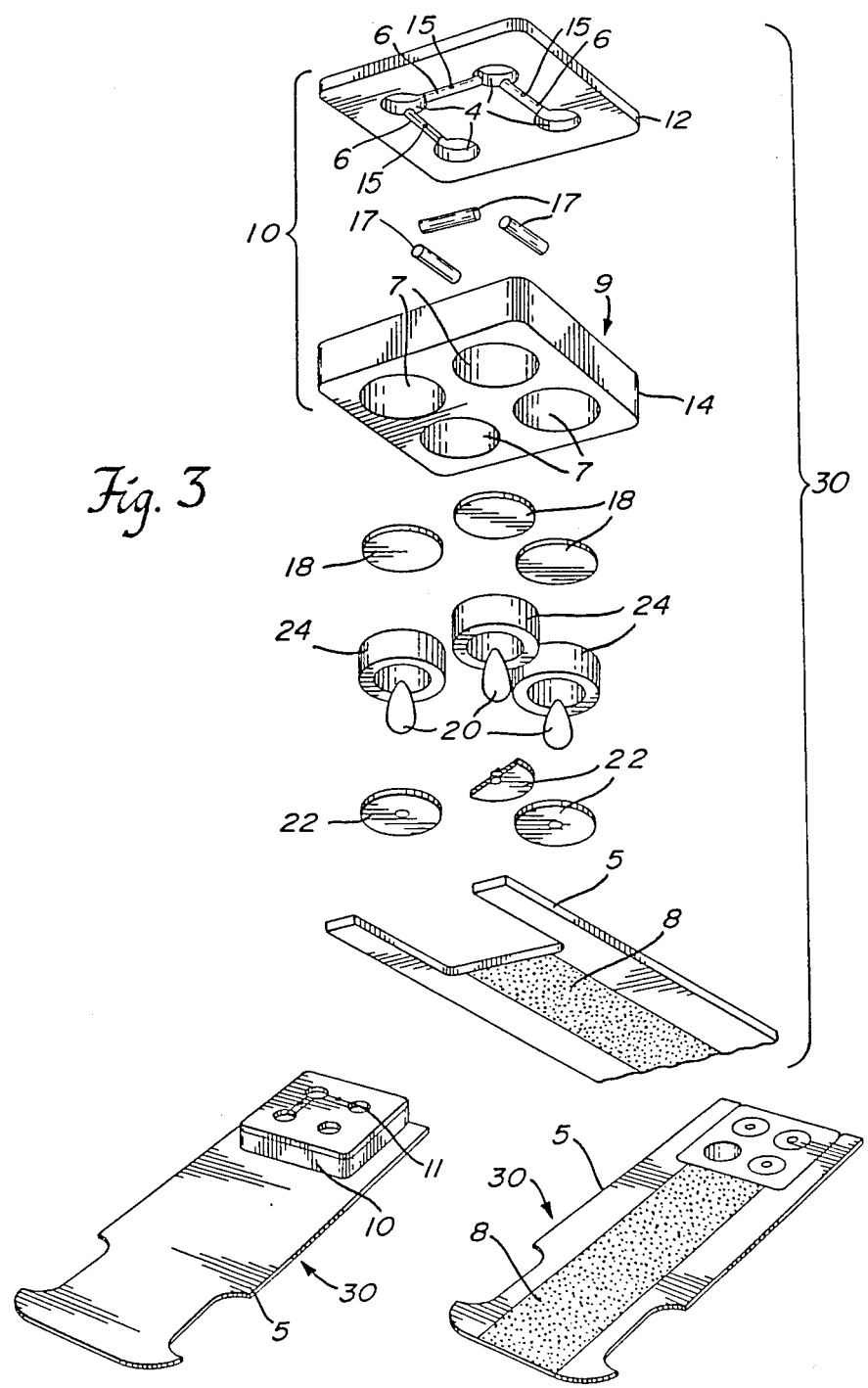

Reference b — c Sample Enzyme
Enzyme         + 
   +           Substrate
Substrate      (immobilized)
(immobilized)

Calibrant a
Enzyme
   +
Substrate
(immobilized)

Calibrant b — A — c Sample
   +                  +
Caffeine           Caffeine

Calibrant a — C — d Sample
   +                  +
Theophylline       Theophylline Calibrant b — c Sample Reference a     d a,b+c each contain creatinium membrane
+ membrane containing glycine hydrochloride

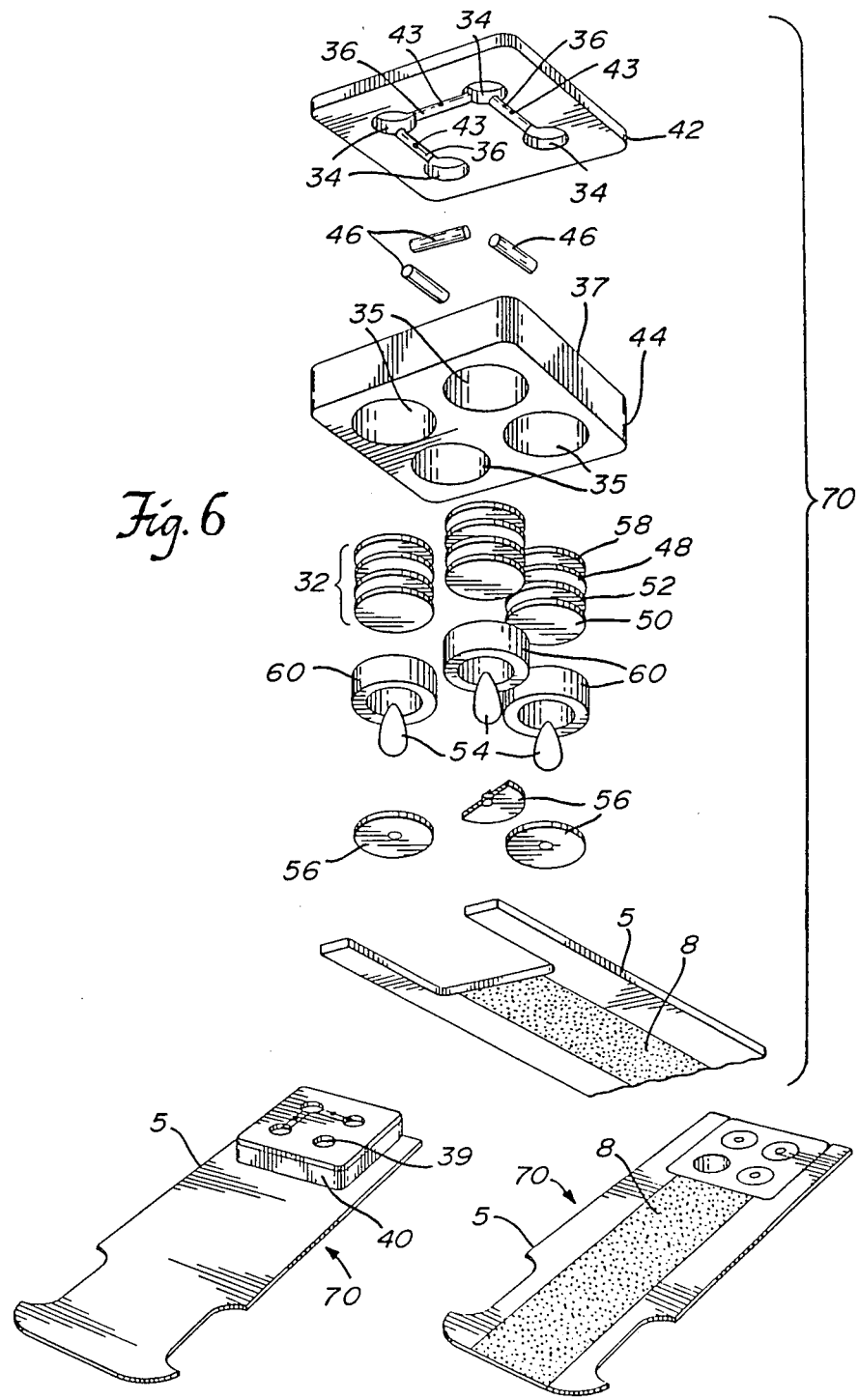

SENSOR HAVING ION-SELECTIVE ELECTRODES

RELATED APPLICATION

This application is a continuation-in-part of U.S. application Ser. No. 750,525, filed on June 27, 1985.

BACKGROUND

Ion-Selective Electrodes

Ion-selective electrodes respond preferentially or selectively to a particular ionic species in a liquid. They are often used in potentiometric measurement of the activity of an ion in a liquid sample. Potentiometric measurement determines the difference in electrical potential between two electrodes which, in contact with a liquid, form an electrochemical cell. The half cell potential of one electrode—the reference electrode—is essentially constant and that of the other electrode—the indicator electrode—varies with the ionic activity of the liquid being analyzed. The electrical potential across the electrodes is proportional to the logarithm of the activity of ions in solution to which the ion-selective electrode responds. The Nernst equation describes the logarithmic relationship. The difference in electrical potential can be determined using a potentiometric measuring device, such as an electrometer.

Several types of ion-selective electrodes are available and include, for example, conventional glass electrodes for pH determinations which are widely used in laboratories. Glass electrodes are based on alkali ion silicate compositions. Electrodes for the determination of pH can be made of lithium silicates or borosilicate glass which is permeable to hydrogen ions ($H^+$) but not to anions or to other cations. If a thin layer of a glass selectively permeable to $H^+$ is positioned between two solutions of different $H^+$ concentrations, $H^+$ ions will move across the glass from the solution of high concentration to that of low $H^+$ concentration. Such movement results in the addition of a positive ion to the solution of low $H^+$ concentration, leaves a negative ion on the opposite side of the glass and produces an electric potential across the glass. Immersion of a pH independent reference electrode into the solution completes the circuit and the potential difference can be measured.

Another type of ion-selective electrode uses liquid ion exchangers and is supported by inert polymers, such as cellulose acetate, or in polyvinyl chloride films. An important example of this type of electrode is a $Ca^{2+}$-responsive electrode which is based on calcium salts of diesters of oil-soluble phosphoric acids. U.S. Pat. Nos. 3,429,785; 3,438,886; and 3,445,365 describe ion-sensitive electrodes which have membranes made of a porous inert substance filled with an ion-exchange organic liquid, which are selectively responsive to divalent cations (e.g., $Ca^{2+}$, $Mg^{2+}$)

Neutral carrier-based sensors for both monovalent and divalent cations are similar to ion-exchanger-based electrodes. Both can involve ion-exchange sites, especially negative mobile sites resulting from mediators or negative fixed sites arising from hydrolysis of support materials. Neutral carriers, which can be cyclic or open-chain, are generally hydrophobic complex formers with cations. Such compounds result in selective extraction, and therefore selective permeability, for $K^+$, $Na^+$ $Ca^{2+}$, which would not otherwise dissolve in the membrane phase as simple inorganic salts. An example of such a carrier is valinomycin, which can be used in electrodes selectively responsive to $K^+$.

Electrodes for the determination of the $H^+$ content of a liquid sample have been described by others. They commonly contain a plastic membrane which has an ion-selective component (an ionophore) and a solvent/plasticizer compound in which the ion-selective component can be dissolved. In addition to glasses selectively permeable to $H^+$ ions, hydrogen ionophores such as lipophilic derivatives of uncouplers of oxidative phosphorylation and lipophilic tertiary amines have been used.

Simon et al, for example, have described a micro pH electrode containing tridodecylamine (($C_{12}H_{25}$)$_3$N or trilauryl amine) as the hydrogen ionophore. *Analytical Chemistry* 53: 2267–2270 (1981). The authors report that this electrode gives excellent response to changes in pH between 5.5 and 12. However, at least two important disadvantages result from the fact that the membrane phase must contain dissolved carbon dioxide ($CO_2$) in order to function properly. First, electrode performance (i.e., $CO_2$ content) may be seriously affected by changes in temperature and pressure. Second, mass production is also very difficult because manufacture must be carried out under carefully controlled conditions; in addition, the dissolved $CO_2$ diffuses out during storage of the electrodes.

Other types of ionophores are based on uncouplers of oxidative phosphorylation in mitochondria. An example is described by Finkelstein. *Biochimica Biophysica Acta*, 205: 1–6 (1970). Weak-acid uncouplers of phosphorylation, such as 2,4-dinitrophenol and m-chlorophenylhydrazone mesoxalonitrile, act as $H^+$ ion carriers. They are, however, unsuitable as components of membranes incorporated into ion-selective electrodes because of their finite water solubilities (i.e., they would not remain membrane bound and would leach out of the membrane).

Brown et al. describe a pH sensor claimed to be suitable for chronic intravascular implantation. The pH-sensitive element is a thin film of an elastomeric polymer which is made ion permselective through the addition of a hydrophobic, lipophilic specific $H^+$-ion carrier. The carrier used is p-octadecyloxy-m-chlorophenylhydrazone mesoxalonitrile (OCPH, which is a higher molecular weight homolog of the weak-acid uncoupler m-chlorophenylhydrazone mesoxalonitrile). Brown and co-workers state that although the OCPH molecule acted as a mobile $H^+$ carrier in a variety of elastomers, pH response characteristics of sufficiently good quality for practical use were only obtained using polymer matrices especially designed for the purpose. U.S. Pat. No. 3,743,588 (1973); O.H. LeBlanc, J. F. Brown et al. *Journal of Applied Physiology*, 40: 644–647 (1976). The preparation of polymers which can be used with the OCPH molecule is described by Vaughn. U.S. Pat. No. 3,189,662 (1965); H. A. Vaughn and E. P. Goldberg, *Polymer Letters*, 7:569–572 (1969).

In U.S. Pat. No. 3,691,047 (1972) Ross and Martin describe an ion-sensitive membrane for potentiometric electrodes. The membrane is described as a gelled mixture in which the solid phase is described as being polymer (e.g., cellulose triacetate) and the liquid phase as an organic ion-exchange material dissolved in an organic solvent (e.g., calcium (bis-dibromoleylphosphate)$_2$ dissolved in dioctylphenylphosphonate). The ion-sensitive electrode is said to have a membrane whose major constituent is an organic ion-exchanger which is dissolved in a non-volatile organic solvent.

In U.S. Pat. No. 4,214,968 (1980), Battaglia et al. describe a dry-operative ion-selective electrode for use in determining ion content of liquids. The electrode is said to be comprised of a dry internal reference electrode in contact with a hydrophobic ion-selective membrane. The internal reference electrode is a dried metal/metal-salt reference half cell or a dried redox couple reference electrode and is wetted upon application of a liquid sample. The ion-selective membrane includes an ion carrier (e.g., valinomycin) which is dissolved in a carrier solvent dispersed in a hydrophobic binder.

In U.S. Pat. No. 4,184,936 (1980), Paul and Babaoglu describe a device for determining ion activity of a liquid sample. The device is described as having an ion-selective membrane which is coated over an internal reference element (made of an electrolyte-containing layer, a metal salt and a metal layer) and a support. The two electrodes of the device are said to be solid and, preferably, dried.

In U.S. Pat. No. 4,053,381 (1977), Hamblen et al. describe another device for measuring ion activity in liquids. The electrodes which are a component of the device preferably include at least one ion-selective electrode in which the internal reference electrode has several layers. The layers include a metal layer, a layer of an insoluble salt of the metal and an electrolyte-containing layer which is preferably dried. The claimed device includes solid electrodes.

At the present time, there are many types of ion-selective electrodes available for the measurement of the ion content of a liquid. These ion-selective electrodes, however, have limitations. These limitations include the requirement for membranes comprised of specially designed polymer matrices; utilization of ionophores which require pre-neutralization with base to improve membrane sensitivity and reduce response time; the need for storage under well-controlled conditions; and loss of sensitivity and reliability during storage. In addition, ion-selective electrodes now available for pH determination require relatively large samples (i.e., 1.0 mL. or more) for accurate operation and are made of glass, which is costly and cannot be incorporated into an electrode suitable for automatic processing of samples of very small size.

There is a need for an ion-selective electrode which can be used to provide accurate, rapid measurement of the ion content of smaller samples (e.g., of microliter size) than those presently available. There is also a need for an ion-selective electrode which can provide an accurate and quicker measurement of other constituents of smaller samples than is possible with presently available electrodes.

Differential Measurement Techniques

The technique of differential potentiometric measurement depends on potential differences arising between two identical electrochemical half-cells immersed in solutions of different activity separated by a salt bridge. The two half-cells together comprise a concentration cell. In the present case the activity of one half-cell ($a_1$) is fixed (reference) while that of the other ($a_2$) (sample) is variable such that the emf of the concentration cell may be defined as:

$$E_1 = E^\circ + \frac{RT}{nF} \ln a_1. \qquad 1$$

-continued $$E_2 = E^\circ + \frac{RT}{nF} \ln a_2. \qquad 2$$

$$E_{cell} = E_2 - E_1 = \frac{RT}{nF} \ln a_2 - \frac{RT}{nF} \ln a_1. \qquad 3$$

$$E_{cell} = \frac{RT}{nF} \ln \frac{a_2}{a_1}. \qquad 4$$

where $\frac{RT}{nF} = 59.1$ mv @ 298° K. for $n = 1$ and, $E_1$ = emf of reference half-cell
$E_2$ = emf of sample half-cell
$E^\circ$ = standard reference electrode potential
R = molar gas constant; 8.314 volt-coulombs/degree(K.)
T = absolute temperature, °K.
n = charge on the ion
F = Faraday constant; 96,493 coulmbs
$a_1$ and $a_2$ = ionic activity of reference sample In the case of a cation such as potassium ($K^+$), if the half-cell $a_1$ is defined as a reference half-cell and assigned a zero potential then the emf of the concentration cell will be positive if $a_2 > a_1$ and negative if $a_2 < a_1$. Since $a_1$ is fixed, the equation for the cell potential contains only one unknown ($a_2$); upon measuring $E_{cell}$ the equation may be solved for $a_2$.

Differential measurement techniques have been used to measure indirectly the concentration or activity of constituents of biological fluids other than $H^+$, including other ions such as sodium ($Na^+$) potassium ($K^+$), calcium ($Ca^{++}$) and chloride ($Cl^-$). In addition, such techniques often make use of biosensors or enzyme electrodes, which include a biological catalyst (e.g., immobilized enzymes, cells, layers of tissue) coupled to an electrode sensitive to a product or co-substrate of the biologically catalyzed reaction. The concentration of enzymes or of substrates can be determined using differential measurement techniques. For example, many enzyme reactions result in the production of an acid or a base. Ionization of the acid or base in turn results in liberation or uptake of $H^+$ and a change in the pH of the solution. The measured change in $H^+$ concentration or pH can be the basis for a stoichiometric determination of the concentration of substances (e.g., glucose, urea, etc.) which liberate or take up hydrogen ions.

In the case of differential pH measurement, each half-cell would contain a pH electrode. The hydrogen ion activity of the $a_1$ half-cell would be fixed and that of $a_2$ (sample) would vary depending on the pH of the sample. The emf measured across the cell by means of an electrometer could then be used to calculate the hydrogen ion activity of $a_2$.

In the case of a differential measurement requiring an enzyme, the enzyme would be placed in either one or both half-cells and the sample would be added to both half-cells or the sample would be added to one half-cell and a calibrator would be added to the other half-cell. As a result, when the enzyme reacts with the substrate in the sample, a decrease or increase in pH occurs; the magnitude of this change is directly proportional to the amount of substrate in the sample. Similarly, a substrate could be substituted for the enzyme and the cell used to measure the enzyme activity of a given sample.

For example, Nilsson and co-workers describe the development of enzyme electrodes in which hydrogen ion glass electrodes are used to make enzyme-pH electrodes for the determination of glucose, urea and penicillin in solutions. The enzymes used for the determination are glucose oxidase, urease and penicillinase, respectively. Nilsson, H. et al., *Biochimica et Biophysica Acta*, 320:529–534 (1973).

Mosca and co-workers also describe the determination of glucose by means of differential pH measurements. The technique is based on the measurement of the change in pH produced by the hexokinase catalyzed reaction between glucose and ATP. They describe two systems said to be useful for determining the difference in pH between two 1-ml. aqueous samples. The concentration of glucose is calculated from the measured change in pH by means of an equation derived by the authors. Mosca, A. et al., *Analytical Biochemistry*, 112:287–294 (1981). Differential measurement of pH to determine glucose in whole blood and plasma and development of an automated system for doing so is subsequently described by this group. Luzzana, M. et al., *Clinical Chemistry*, 29:80–85 (1983).

The same apparatus and a differential pH technique are described for use in measuring lipase activity of biological fluids such as serum, plasma and duodenal juice. Ceriotta, F. et al., *Clinical Chemistry*, 31:257–260 (1985). A refinement in the differential pH measurement technique is said to serve as the basis for the determination of urea, creatinine and glucose in plasma and whole blood. The enzymes urease, creatinine iminohydrolase and hexokinase, respectively, are used for the determinations. The concentrations of the three substrates are calculated based on the observed changes in pH of the solutions after reactions have occurred.

In U.S. Pat. No. 4,353,867 (1982), Luzzana describes a method and apparatus for the determination of substances, such as glucose, urea and enzymes in biological solutions (e.g., blood, serum, urine). The method uses differential pH measurement in which two glass pH electrodes are placed in separate solutions; the change of pH in the solutions after reagents are added is determined; and the concentration of the substance of interest is calculated from the observed pH change. The apparatus is comprised of a sample cuvette; a cell having two glass capillary electrodes; a means for measuring pH at the two electrodes; and an electronic means for calculating the concentration of the substance from the pH measurements.

Immunosensors

Electrochemical immunosensors may be described as either potentiometric or amperometric. Potentiometric immunosensors may be used to measure either antibodies or antigens. They may be described as either direct or indirect and can be either membranes or solid electrodes. An example of a direct potentiometric immunosensor for the determination of an antigen is described by Yamamoto, et al. An antibody, anti-hCG, is immobilized on a titanium wire. The anti-hCG electrode and a reference electrode are placed in a buffer solution. The antigen, hCG, is added and as the antigen binds to the immobilized antibody, the potential difference between the two electrodes changes until equilibrium is attained. The equilibrium potential difference is directly proportional to the concentration of the antigen. Yamamoto, et al., *Clinical Chemistry*, 26: 1569–1572 (1980). The exact nature of the potentiometric response is not fully understood, but it is generally acknowledged to involve a surface charge neutralization or redistribution.

Another example of a direct potentiometric immunosensor for the determination of an antibody is described by Keating and Rechnitz. This type of immunosensor responds to specific antibodies through modulation of a background potential, fixed by a marker ion, in such a manner that the potential change is proportional to the concentration of antibody. An immunosensor for the determination of digoxin antibody is described wherein digoxin is coupled to the marker ion carrier molecule benzo-15-crown-5. The resulting conjugate is incorporated into a polyvinylchloride membrane. Keating, M. Y. and Rechnitz, G., *Analytical Chemistry*, 56: 801–806 (1984). An antibody-selective potentiometric electrode for antibody determination is also described by Rechnitz and Solsky in U.S. Pat. No. 4,402,819. A serious limitation to the routine clinical use of this method is the necessity of maintaining a constant background level of the marker ion such that biological samples would have to by dialyzed before analysis.

Indirect potentiometric immunosensors are enzyme linked and are analogous to other enzyme immunoassay methods except that the electrochemical sensor is used to measure the product of the enzymesubstrate reaction. Both homogeneous and heterogeneous potentiometric enzyme immunoassays have been described. For example, Boitieux and coworkers describe a heterogeneous potentiometric enzymelinked immunoassay for the determination of estradiol. Boitieux et al., *Clinical Chemica Acta*, 113: 175–182 (1981). The antibody to estradiol is immobilized onto a porous gelatin membrane. The membrane is incubated with peroxidase-labelled estradiol and free estradiol. After washing, the membrane is fixed onto an iodide sensitive electrode. The peroxidase activity is determined in the presence of hydrogen peroxide and iodide ion. The iodide selective electrode potential is a function of the estradiol concentration.

A homogenous potentiometric enzyme immunoassay for human IgG has been described by Fonong and Rechnitz. The method is based on the inhibition, by IgG, of $CO_2$ production by beta-ketoadipic acid catalyzed by chloroperoxidase enzyme conjugated to IgG antibody. Fonong and Rechnitz, G., *Analytical Chemistry*, 56: 2586–2590 (1984). If the enzyme-IgG conjugate is incubated with a sample containing the antigen (IgG) before reaction with the enzyme substrate, the observed rate of $CO_2$ liberation, measured with a potentiometric $CO_2$ gas-sensing electrode, will be decreased. The decrease in activity is proportional to the concentration of IgG in the sample.

Amperometric enzyme immunosensors are analogous to the potentiometric immunosensors except that an amperometric sensor, usually an oxygen electrode, is used to measure enzyme activity. For example, Aizawa, Morioko and Suzuki have described an amperometric immunosensor for the determination of the tumor antigen alpha-fetoprotein (AFP). Aizawa et al., *Analytica Chimica Acta*, 15: 61–67 (1980). Anti-AFP is covalently immobilized on a porous membrane. The membrane is incubated with catalaselabelled AFP and free AFP. After competitive binding the membrane is examined for catalase activity by amperometric measurement of oxygen after addition of hydrogen peroxide. In a similar manner, Boitieux and co-workers describe an amperometric enzyme immunoassay for the determination of hepatitis B surface antigen. Boitieux et al., *Clinical Chemistry*, 25: 318-321 (1979).

A limitation of enzyme-linked amperometric sensors is the necessity of synthesizing the enzyme conjugates and the high cost of currently available amperometric sensors such as oxygen electrodes.

DISCLOSURE OF THE INVENTION

The present invention is a sensor for the potentiometric determination of the ion content or activity of a sample and the concentration of other components of a sample through the use of ion-selective electrodes. The sensor is especially suited for rapid determination of the hydrogen ion content or pH of biological fluids; the concentration of other ions in biological fluids; and, through differential pH measurements or immunoassay techniques, the concentration of other components (e.g., glucose, urea, triglycerides, uric acid enzymes such as aspartate aminotransferase (AST), alanine aminotransferase (ALT), amylase, creatinine kinase (CK), alkaline phosphatase and drugs) of biological fluids. It is particularly useful for automated handling or processing.

The sensor is comprised of ion-selective electrodes which are held in a frame and have porous material (e.g., microporous polyethylene such as that manufactured by Porex Technologies Corp.) between them. The porous material provides a means for ionic flow between the electrodes once a sample is applied at the electrodes. The ion-selective electrodes are comprised of a membrane which is selectively permeable to the ion or other substance whose concentration is to be determined and a reference electrode. The membrane does not require preconditioning before use.

The selectively permeable membrane is comprised of an ion-selective compound (or ionophore) and a thermoplastic resin or a plastic material, which can all be dissolved in an organic solvent. In addition, it can also include a plasticizer. The ion-selective component for a pH sensor is a compound having the following general formula:

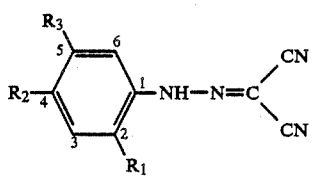

wherein $R_1$, $R_2$ and $R_3$ are independently selected and each can be: (1) a halogen; (2) an alkyl group having from 4-18 carbon atoms; (3) a halogen-substituted alkyl group; (4) an alkoxy group; (5) a halogen-substituted alkoxy group; (6) an acid group represented by —$CO_2R_4$ wherein $R_4$ is alkyl having 1-18 carbons; (7) a keto group represented by —$COR_5$ wherein $R_5$ is selected from the groups defined for $R_4$; or (8) a hydrogen atom.

In an embodiment of the present invention, the membrane comprises an organic plastic matrix, polyvinyl chloride (PVC), which contains the ion-selective compound 2-octadecyloxy-5-carbethoxyphenylhydrazone mesoxalonitrile. The ion-selective compound, the PVC and a plasticizer, which in this embodiment is 2-nitrophenyloctylether, are all soluble in the solvent tetrahydrofuran (THF). These components comprise the membrane formulation.

In a preferred embodiment, the membrane comprises about 10-40% PVC by weight, and its thickness is greater than 1 mil. In a particularly preferred embodiment, the membrane is made of about 20-35% PVC by weight and is about 3-15 mils thick. The membrane which is described can be used as a component of the ion-selective electrode of the present invention. It can also be incorporated into commercially available electrode bodies.

The sensor of this invention also has an internal reference element or material which includes a known concentration of the sample component whose concentration is to be determined.

BRIEF DESCRIPTION OF THE DRAWINGS

FIG. 1 is a perspective view of the top of a sensor having ion-selective electrodes and a handle which has a magnetic stripe in which data is recorded.

FIG. 2 is a perspective view of the bottom of a sensor having ion-selective electrodes and a handle which has a magnetic stripe in which data is recorded.

FIG. 3 is a perspective view showing the individual components of a sensor which can be used to determine the hydrogen ion activity (pH) of a sample or the concentration of other ions in a sample.

FIG. 6 is a perspective view showing the individual components of a sensor which can be used to determine the activity or concentration of a component of a sample by a differential measurement technique. FIG. 6A is a perspective view of the top of the sensor FIG. 6, which has a handle which has a magnetic stripe in which data is recorded. FIG. 6B is a perspective view of the bottom of the sensor of FIG. 6.

BEST MODE FOR CARRYING OUT THE INVENTION

Figure 4A:
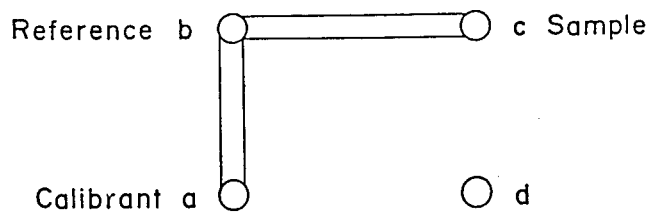
FIG. 4a-4m present schematic representations of ion selective electrode configurations.

The sensor which is the subject of this invention is used for the potentiometric determination of the ion content of a sample or the concentration of other components of a sample. It is particularly useful in the rapid determination of the hydrogen ion activity (or pH) of or concentration of other ions in a biological fluid (e.g., blood) and in measuring concentrations of other components (e.g., glucose, urea, triglycerides, uric acid, enzymes such as aspartate aminotransferase (AST), alanine aminotransferase (ALT), amylase, creatine kinase (CK), alkaline phosphatase and drugs) in biological fluids. Ionophores selective for sample components and incorporated into ion-selective membranes of such sensors are also the subject of this invention.

The sensor can now be further described with reference to the figures.

FIGS. 1 through 3 show a sensor having ion-selective electrodes and a handle having a magnetic stripe in which data are recorded. The sensor represented in these figures can be used to determine the hydrogen ion content or pH of a sample or the concentration of other ions in a sample. These figures will now be referred to in describing a sensor to be used for the determination of hydrogen ion content of a sample. It is to be understood, however, that the sensor can be used for determination of other ions or other components as well.

The sensor 30 is comprised of ion-selective electrodes which are held in a frame or body 10 which has upper section 12 and lower section 14. In addition, the sensor 30 has a handle 5 bearing a magnetic stripe 8 on its lower surface.

Upper section 12 of frame 10 has four openings 4 and three grooves 6, which are positioned between the openings. Lower section 14 of frame 10 has four openings 7 and three grooves (not shown) positioned between the openings. Upper section 12 and lower section 14 are in such a relationship that openings 4 and openings 7 are aligned and grooves 6 in the upper section and the grooves in the lower section are aligned. As a result, openings 4 and 7 form four openings 11 and grooves 6 of the upper section and the grooves in the lower section define spaces between three of the openings 11. Upper section 12 has small holes 15 located between openings 4. Holes 15 allow the passage of air. The ion-selective electrodes are located within the openings 11 and are connected by a porous material 17 which is cylindrical or rod shaped and provides a means for ionic flow between the electrodes upon the application of a sample at the electrodes. The cylindrical or rod-shaped porous material 17 is located in the spaces between openings 11. Upper section 12 and lower section 14 are sealed, for example by being ultrasonically welded under pressure, such that there is no leakage of sample or solutions onto porous material 17 or between or into the two sections of frame or body 10.

As shown in FIG. 3, sensor 30 has four positions at which ion-selective electrodes can be located. Although there will generally be an ion-selective electrode at each of these positions, these can be used in various combinations depending on the analytical information desired. Accordingly, the position of grooves 6 in upper section 12 and the grooves in lower section 14 will vary as needed for the analysis being carried out. For example, grooves 6 in upper secton 12 can be positioned as shown in FIG. 3; the grooves in lower secton 14 will be positioned so that spaces will be defined between the three electrodes, as described above, when upper section 12 and lower section 14 are joined. Alternatively, two grooves 6 can be positioned in parallel to one another in upper section 12 and the grooves in lower section 14 positioned correspondingly. Two, three or all four electrodes can be used. Porous rods 17 can be hydrophilic and conductive or hydrophobic and nonconductive. The use of conductive or nonconductive material between a pair of electrodes is determined by the analyses to be carried out. The various combinations of membranes are best described by example.

In the first example, as represented in FIG. 4a, three membranes are active and all three contain the same membrane. Positions a and b have known concentrations of the ion to be determined and position c has the sample, which has an unknown concentration of the ion of interest. The emf developed between the solutions in a and b can be used to calibrate the sensor; the slope value is then used to determine the concentration of the sample from the emf developed between the solutions in b and c. In addition, because the concentrations of ions in a and b are known, it is possible, using predetermined slope values, to calculate what the potential difference between a and b should be and to compare this value with the measured potential difference or to calculate a concentration for a and determine how this varies from the known value. In a clinical chemistry sense, the solution in a would then be used as a control.

Figure 4B:
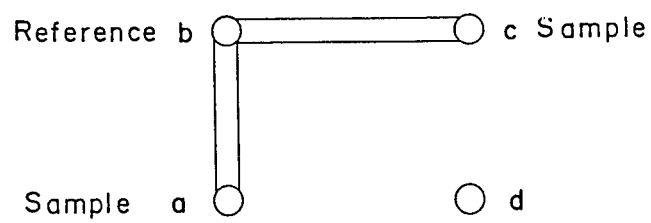

The a, b, c configuration can also be used in such a manner that replicate samples can be analyzed. This is represented in FIG. 4b. In this case the same sample is placed in positions a and c and reference solution in b. Using a predetermined slope value, it is possible to determine simultaneously two values for the same sample.

Figure 4C:
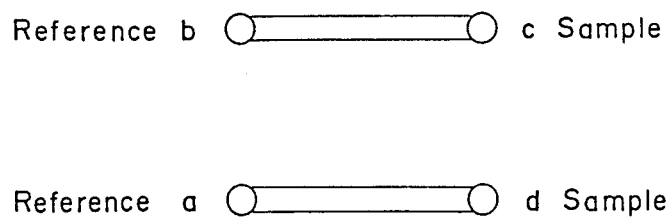

It is also possible to determine simultaneously two different analytes. This is represented in FIG. 4c. For instance, a and d can be membranes selective for one analyte and b and c can be membranes selective for another analyte. Useful combinations might be sodium/potassium, pH/calcium, glucose/urea and urea/creatinine. In these instances predetermined calibration data are required.

Figure 4D:
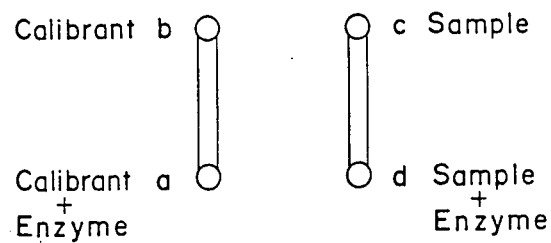

An enzyme/substrate sensor can be constructed as represented in FIG. 4d. In this case, a, b, c and d can all be the same membrane; for example, they can all be for determination of pH. However, a and d would contain, in addition to the pH membrane, an immobilized enzyme. An unknown analyte sample concentration is added to both c and d; a known concentration of the same analyte is added to a and b. The enzymes in a and d act on the substrate and produce a pH change proportional to the concentration of the analyte in the sample. If it is assumed that all the membranes are identical, the emf developed between a and b (the reference solution) can be used to calibrate the electrodes. The calibration data obtained for a and b may then be used to calculate the sample concentration in c and d.

Figure 4E:
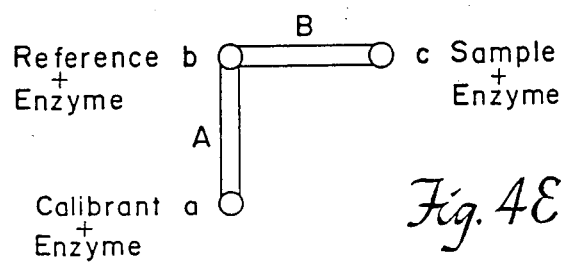
Figure 4F:
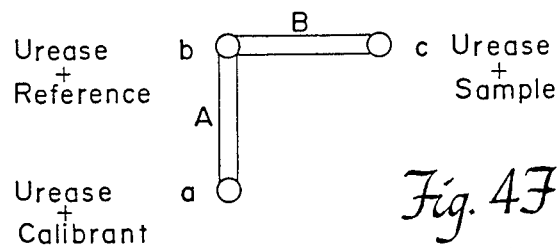
Figure 4G:
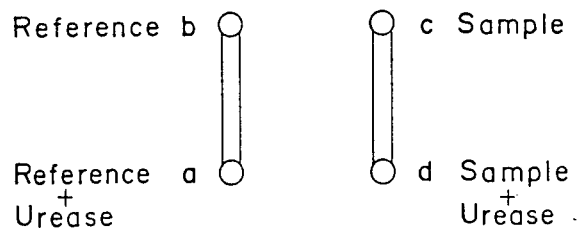
Figure 4H:
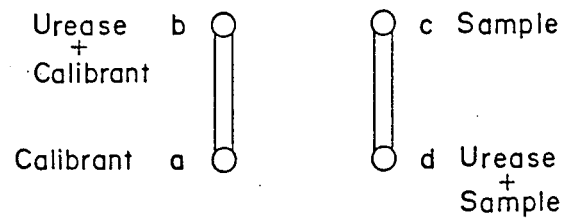
Figure 4I:
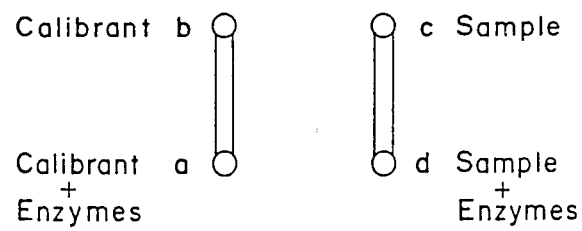
Figure 4J:
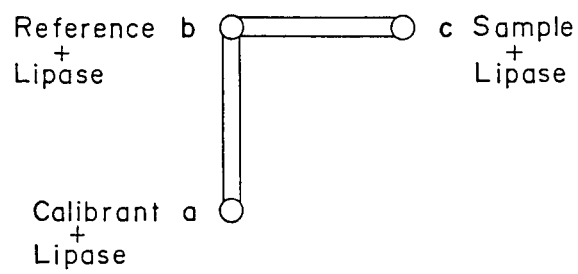
Figure 4K:
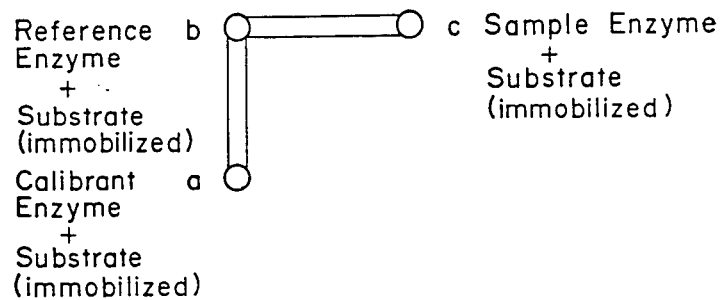

An enzyme/substrate sensor can be constructed as represented in FIG. 4k. In this case, a, b and c can all be the same membrane; for example, they can all be for determination of pH. However, a, b and c contain, in addition to the pH membrane, an immobilized substrate. The substrate concentrations in a and b are different; the concentration of substrate in c can be the same as in a and b or can be different. An unknown analyte enzyme sample concentration is added to c; a known concentration of the enzyme to be measured is added to a and b. The enzymes in a, b and c act on the substrate in a, b and c and produce a pH change proportional to the concentration of the enzyme in the sample. If it is assumed that all the membranes are identical, the emf developed between a and b (the reference solution) can be used to calibrate the electrodes. The calibration data obtained for a and b may then be used to calculate the enzyme sample concentration in c.

Examples of substrates which can be immobilized in an enzyme/substrate sensor such as that represented in FIG. 4k are: amino acids such as L-alanine and L-aspartate, creatine and starch. These can be used, respectively, for the determination in a sample of: alanine aminotransferase, aspartate aminotransferase, creatine kinase and amylase. As described in Example 8, an enzyme/substrate such as that represented in FIG. 4k can also be used to determine the creatine concentration of a sample.

If one were using a kinetic rate method, this methodology, in effect, allows one to "calibrate out" any temperature effects on the enzymatic reaction rates. In the case of an endpoint or equilibrium measurement, effects of temperature in the Nernst equation could be normalized.

The porous rods 17 between the electrodes can be conductive or nonconductive; the use of conductive or nonconductive material between a pair of electrodes is determined by the analysis to be carried out.

The porous material can be of a microporous plastic such as nylon, polypropylene, polyethylene, polyvinylidene fluoride, ethylene-vinyl acetate, styrene-acrylonitrile or polytetrafluoroethylene. The porous material can also be cellulosic in nature such as rolled filter paper or longitudinal fiber bundles. In one embodiment the porous material consists of crylindrically-shaped pieces of ultrahigh molecular weight microporous polyethylene (POREX Technologies, Fairburn, GA). This material is by nature hydrophobic such that it will not wet with water.

The porous material can be rendered hydrophilic by soaking it in a solution (about 0.1% to 0.6% by volume) of a surfactant. Surfactants which have been found to be useful are the nonionic surfactants such as the octylphenoxypolyethoxyethanol family of surfactants which includes Triton X-100 (Rohm & Haas Co.), polyoxyethylene ethers such as Brij 35, polyoxyethylene sorbitan derivatives such as Tween 20, fluoraliphatic polymeric esters such as 3M's Fluorad FC-171 and surfactants such as Sherex Chemical Co.'s Arosurf 66 PE-12. Anionic and cationic surfactants can also be used. The porous material without wetting agent or surfactant is nonconductive. The absence of porous material between two electrodes results, of course, in nonconductivity.

The ion-selective electrodes are comprised of an ion-selective membrane 18 and a reference electrode 22 which is a silver/silver chloride material. The ion-selective membrane 18 is made of an ion-selective compound (an ionophore), a thermoplastic resin and a plasticizer, all of which are soluble in an organic solvent. It is held in place in the ion-selective electrode by a retainer means, such as retainer ring 24. There is, thus, a mechanical seal between the retainer means and the lower section of the sensor body such that there can be no leakage from the membrane. An important characteristic of the sensor is that the ion-selective membranes incorporated in it do not require preconditioning (e.g., soaking in a solution of the ion to be measured) before the sensor can be used.

In the case of the hydrogen ion-selective membrane, the ion-selective compound which is incorporated into the membrane has the general formula:

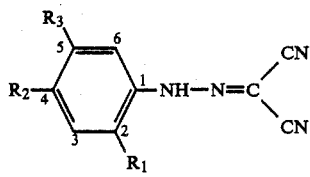

In this compound, $R_1$, $R_2$ and $R_3$ represent components of the compound which can be the same or different. $R_1$, $R_2$ and $R_3$ can be: (1) a halogen; (2) an alkyl group having 4–18 carbon atoms; (3) a halogen-substituted alkyl group; (4) an alkoxy group; (5) a halogen-substituted alkoxy group; (6) an acid group represented by —$CO_2R_4$ wherein $R_4$ is an alkyl having 1–18 carbon atoms; or (7) a keto group represented by —$COR_5$ wherein $R_5$ is selected from the groups defined for $R_4$; or (8) a hydrogen atom.

Derivatives of this general formula which are particularly preferred as components of the hydrogen-ion-sensing membrane include:

a. 2-trifluoromethyl-4-octadecyloxyphenylhydrazone mesoxalonitrile

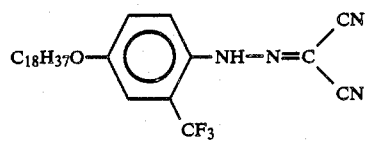

b. 2-octadecyloxy-5-trifluoromethylphenylhydrazone mesoxalonitrile

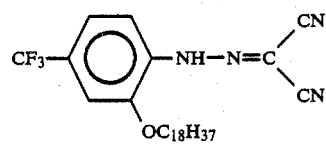

c. 2-octadecyloxy-5-carbethoxyphenylhydrazone mesoxalonitrile; and

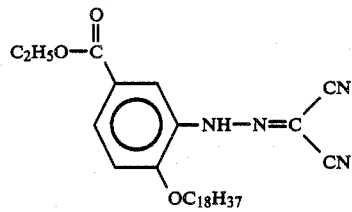

d. 2-octadecyloxy-4-fluorophenylhydrazone mesoxalonitrile.

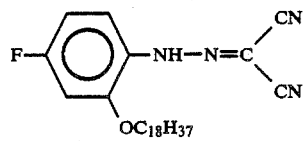

Membranes in which the ion-selective compound is carbethoxyphenylhydrazone mesoxalonitrile are particularly useful in that they exhibit response times of one minute or less; yield stable potentials and exhibit slopes on the order of 57–59 mv per decade change in hydrogen ion concentration and do not require any preconditioning. It is not clear why such membranes have excellent performance characteristics. However, it might be attributable to the presence of an electron-withdrawing ester group meta to the anilino group and its proton, which is apparently more acidic and, therefore, more easily exchanged.

In addition to the ion-selective compound described above, the ion-selective membrane 18 of this invention also comprises a plastic or a thermoplastic resin and, optionally, a plasticizer. The plastic used can be any plastic which can be used to form a film by solvent casting. For example, the plastic can be polyvinyl chloride, polyvinyl acetate, silicone rubber or cellulose acetate. This membrane component serves the purpose of providing support and form to the membrane, and acts as a matrix into which the ion-selective compound is incorporated. In addition, it serves as a barrier to water because it is a hydrophobic material. In one embodiment, the thermoplastic resin used in the membrane is polyvinyl chloride. Others which can be used include: cellulose acetate, polyvinyl acetate and silicone rubber.

The plasticizer, which is an optional component of the membrane, can be any nonvolatile material suitable for the general purpose of facilitating the compounding or production of the membrane formulation and improving the membrane's flexibility. It also contributes to the dissolution of the ionophore. It can be, for example, one or more of the following, used alone or in combination: phthalates; adipates; sebacates; aliphatic and aromatic ethers; aliphatic and aromatic phosphates; aliphatic and aromatic esters; and nitrated aliphatic and aromatic ethers. In one embodiment of this invention, the plasticizer is 2-nitrophenyloctylether.

The components of the ion-selective membrane 18 can be present in varying amounts. The plastic used can comprise about 10–30% by weight of the membrane and in one embodiment is about 28% by weight. The ion-selective compound can be from about 1% to about 10% by weight of the membrane and in general will be about 3% to about 6% by weight. The plasticizer can be from about 50% to about 80% by weight of the membrane and generally comprises about 70% by weight.

The ion-specific membrane 18 incorporated into the ion-selective electrodes of this invention will generally be of a thickness greater than 1 mil and preferably will be from about 3 to about 15 mils in thickness.

The ion-specific membrane of this invention can be made by at least two different methods: solvent casting and dip coating. Solvent casting is illustrated in Example 2 and in general includes the following steps:

1. preparation of the hydrogen ion-specific compound by: (a) alkylation of a nitrated phenolic material to produce an ether; (b) reduction of the nitro group to an amino group; (c) precipitation of the hydrochloride salt of the amine; and (d) conversion of the hydrochloride salt to the mesoxalonitrile derivative;
2. dissolution of the ion-specific compound; a plasticizer and a plastic material in a volatile (organic) solvent; and
3. removal of the volatile organic solvent (e.g., by evaporation).

Figures 5, 5A:
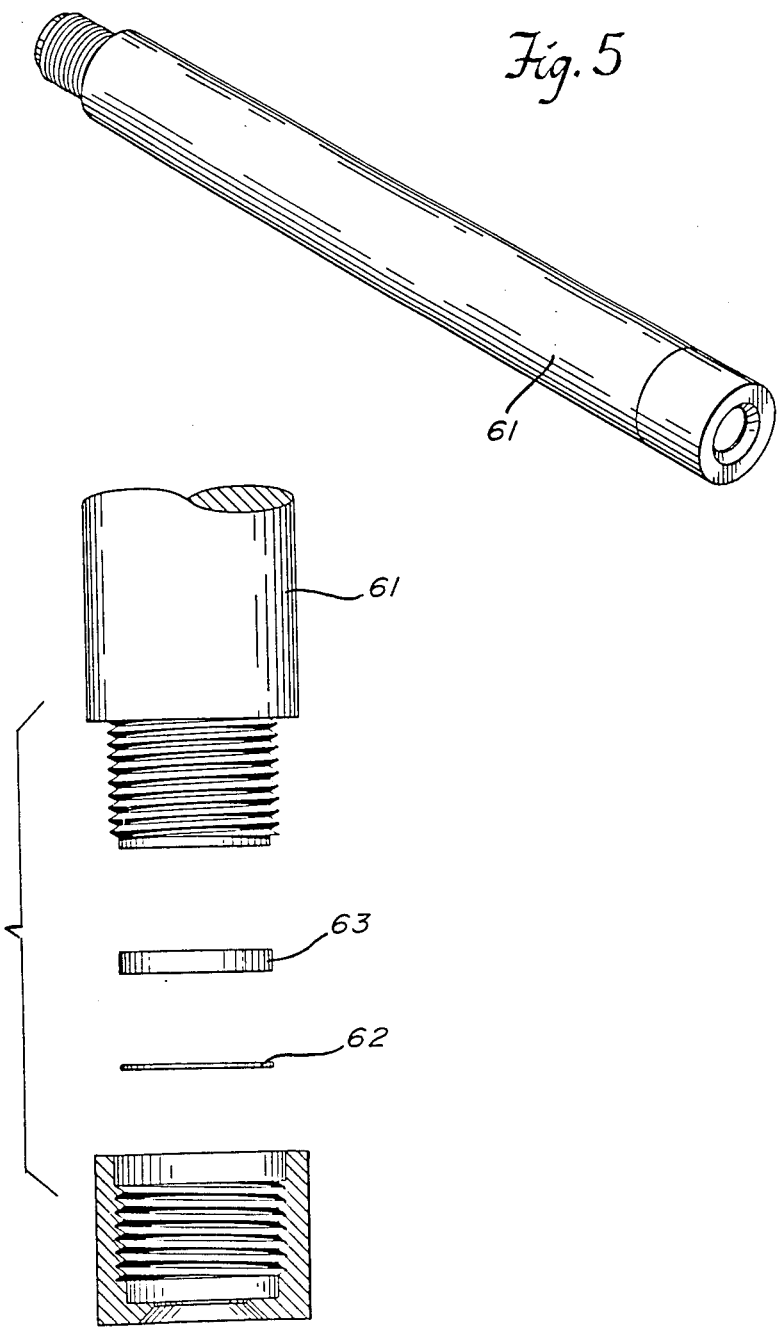
FIG. 5 shows a commercially available barrel-type electrode into which an ion-selective membrane of the present invention can be inserted.
FIG. 5A shows an ion-selective membrane of this invention inserted into the commercially avaliable barrel-type electrode.

After the membrane has been formed, it is shaped (e.g., by cutting, use of a punch-type instrument, etc.) into an appropriate configuration and incorporated into an electrode body, such as the electrode body of the present invention or an Orion electrode body as represented in FIG. 5. This is shown in FIG. 5A.. (Orion Research, Inc., Cambridge, Mass. catalogue #950015). FIG. 5 shows the Orion-electrode body 61 with the ion-selective membrane 62 of this invention, held in the electrode by means of an O-ring 63. A second O-ring (not shown) prevents sample leakage around the membrane.

The ion-selective membrane can also be formed by means of a dip coating or a continuous coating process method. In this method, a base material, such as a nylon mesh or a polyester mesh (e.g., Pecap 355, Tetko, Inc., Elmsford, N.Y.)) is placed in a solvent bath (e.g., ketone, such as 4 methyl-2 pentanone) and the air trapped within the mesh removed. This can be done, for example, ultrasonically using a Branson ultrasonic cleaner; treatment takes about 10–15 seconds. While still wet with solvent, the mesh is placed in the membrane formulation; after it is removed, it is scraped to remove excess formulation. The mesh containing the formulation is then dried; this can be done, for example, at room temperature or in warm air (e.g., 35°–50 °C.).

The internal reference material 20 consists of a solution of the salt of the ion to be determined. The counter ion consists of chloride if the reference electrode is silver/silver chloride. A gelling agent such as agar or agarose can be used to fix the reference material in place. In the case of the pH sensor, the reference material is a buffer solution. In one embodiment, the pH reference material consists of 50 ml glycerol, 50 ml of an aqueous solution consisting of pH 7.4 phosphate-buffered saline (SIGMA Chemical Co., St. Louis, Mo.) and 2.0g of agar. The mixture is heated to dissolve the agar and then placed in the well behind the membrane. After a period of time, normally 5–10 minutes, the mixture gels. For a potassium sensor the aqueous solution can be 50 ml of 0.2M KCl; for the sodium and chloride sensors, the aqueous solution can be 0.2M NaCl.

To modify the sensor of FIGS. 1–3 for the determination of other ions, it is necessary to change at least one of the membrane components and to modify the internal reference material to include the ion to be determined. For example, for potassium determinations, the membrane would include an ionophore specific for potassium, such as valinomycin, a crown ether derivative of benzo-15-crown-5 or some other neutral carrier. The internal reference material would consist of a potassium chloride solution with or without a gelling agent.

To modify the sensor of FIGS. 1–3 for the determination of sodium, the membrane would include an ionophore for sodium, such as monensin, a crown ether derivative of benzo-12-crown-4 or some other sodium neutral carrier (e.g., as described by Simon et al., *Analytical Chem.*, 51: 351–353 (1979)). The internal reference material would include sodium chloride.

To modify the sensor of FIGS. 1–3 for the determination of chloride, the membrane would include an ionophore for chloride such as the quaternary ammonium salt Aliquat 336. The internal reference material would include chloride ion.

As mentioned previously, sensor 30 has a handle 5 which has a magnetic stripe 8. This stripe is very similar to the stripes commonly found on credit cards and bears data recorded onto the stripe at the time of manufacture. The data includes, for example, the following information:

1. Test type: A unique two digit number identifies each specific type of test card (i.e., each specific analyte). This eliminates the need for operator entry of test type information and consequently eliminates possibilities of error.
2. Calibration constant: Three digit numerical constant used in an equation stored in the instrument memory to calculate analyte concentration based on the measured signal. This constant may be used in conjunction with the simultaneous calibration to determine possible test card failure.
3. Expiration date: Four digit code that enables the instrument to determine the expiration date of the test card and ensure that no out-of-date cards are used. The format for this constant is YYWW where YY is the last two digits of the year (e.g., 85 for 1985), and WW is the week of the year (e.g., the week of May 5 through May 11 is week 19).
4. Reserved: Four digits are reserved for future use. In addition to the data described above the following "housekeeping" data can be written on the card:
1. Leader: Minimum of 15 "0"s for synchronization of the instrument magnetic stripe reader circuitry.
2. Start sentinel: Special character used to signify the start of data.
3. LRC: Longitudinal Redundancy Check used in conjunction with a parity bit attached to each data character to detect possible errors in reading data from the magnetic stripe.

An independent function of the magnetic stripe is to prevent reuse of the disposable test cards which are designed for single use only. This is accomplished by destroying the coded information as the test card is removed from the instrument. The error checking functions described above will reject the card if an attempt is made to reuse it.

FIG. 6 shows a sensor of the present invention which can be used to determine the activity or concentration of components of samples by means of a differential measurement technique.

FIG. 6A is a perspective view of the top of the sensor of FIG. 6; FIG. 6B is a perspective view of the bottom of the sensor of FIG. 6. Components of biological fluids (e.g., blood, serum, plasma, urine, saliva, cerebrospinal fluid) which can be measured include, for example, glucose, urea, triglycerides, creatinine, lipase, uric acid and other enzymes (e.g., alanine aminotransferase (SGPT or ALT); alkaline phosphatase (ALP); creatine kinase (CK) and aspartate aminotransferase (SGOT or AST)).

The sensor 70 is comprised of ion-selective electrodes, which are held in a frame or body 40 which has an upper section 42 and a lower section 44. Upper section 42 of frame 40 has four openings 34 and three grooves 36, which are positioned between the openings. Lower section 44 of frame 40 has four openings 35 and three grooves positioned 1 between the openings. Upper section 42 and lower section 4 are in such a relationship that openings 34 and openings 35 are aligned and grooves 36 of the upper section 42 and the grooves in the lower section 44 are aligned. As a result, openings 34 and openings 35 form openings 39 and grooves 36 of the upper section 42 and the grooves in the lower section 44 define spaces between three of the openings 39. Upper section 42 has small holes 43 located between openings 34. Holes 43 allow air to enter space 41.

The ion-selective electrodes are located within the openings 39 and are connected by a porous material 46 which is cylindrical or rod shaped. Porous material 46 provides a means for ionic flow between the electrodes upon the application of a sample at the electrodes. The cylindrical or rod-shaped porous material 46 is located in the spaces 41 between openings 39.

As described for the sensor of FIGS. 1—3, fewer than or more than the four ion-selective electrodes depicted in FIG. 6 can be used. Also as previously described, the porous material between the electrodes can be hydrophilic or hydrophobic; the type of analysis determines this characteristic. For example, if an enzyme substrate is to be measured using the sensor represented in FIG. 6 and a reference sample is to be used, then the configuration could be as shown in FIG. 4d.

The ion-selective electrodes are comprised of a layer 48 having enzyme or substrate immobilized on it; an ion-selective membrane 50; a membrane 52 placed between the two; an internal reference material 54 and a reference electrode 56. There can be an additional membrane 58 in proximity with layer 48.

The ion-selective membrane can be selective for $H^+$ or ammonium ions ($NH_4^+$), as in the case of a urea electrode. In the case of the ammonium-selective membrane, the ionophore is an ammonium-selective material such as nonactin. The ion-selective membrane is held in place in the ion-selective electrode by a retainer means, such as retainer ring 60.

Layer 48 has at least one enzyme or substrate immobilized on it. Layer 48 can be, for example, a nitrocellulose membrane (e.g., type AE100, Schleicher and Schuell, Inc. Keene, NH) having a thickness of about 180 microns. It can also be made of nylon, cellulose, cellulose acetate, glass fiber or any porous material which can serve as a solid support for the immobilization of the enzyme or substrate. The enzyme or substrate can be immobilized by physical restraint (e.g., adsorption onto the solid phase) or by chemical restraint (e.g., covalent attachment or crosslinking).

Layer 48 is separated from the ion-selective membrane 50 by means of a membrane 52, which is generally thin (e.g., less than 20 microns thick) and can be, for example, a dialysis membrane (e.g., Spectra Por 2, Spectrum Medical Industries, Inc., Los Angeles). Membrane 52 serves the purposes of, for example, preserving the activity of the immobilized enzyme of layer 48 by preventing the migration of components of the ion-selective membrane 50 into layer 48; migration might cause denaturation or inactivation of the enzyme.

Membrane 58 is optional and its presence will be determined by what component of a sample is being measured and/or how that component is being measured. The function of membrane 58 is to aid in the physical restraint (immobilization) of the enzyme or substrate of layer 48 and/or to serve as a diffusional barrier to the substrate. For example, to measure the concentration of a substrate of the enzyme immobilized in layer 48, it may be desirable to make a kinetic measurement, rather than an end point measurement. To extend the range of linearity for a kinetic measurement, it is necessary that the enzyme reaction be diffusion limited. In this instance membrane 58 will serve both purposes. If, however, an end point measurement is desired a diffusional barrier would not be required and membrane 58 is not needed. Membrane 58 can be made of regenerated cellulose (dialysis membrane) or other ultrafiltration or reverse osmosis membranous material which can serve as a diffusional barrier to the substrate.

The internal reference material 54 is comprised of a buffer solution. In one embodiment, it is comprised of a filling solution of pH 7.4 phosphate buffered saline. In a preferred embodiment, it is a gel comprised of about 50 ml. pH 7.4 phosphate buffered saline, about 50 ml. glycerol and about 2.0 g agarose.

Reference electrode 56 is an electrode with a fixed potential which exhibits no variation in liquid junction potential when the sample solution is varied or replaced by a calibrating solution. The main requirements for satisfactory reference electrode performance are reversibility (in the electrochemical sense), reproducibility and stability. Three types of reference electrode systems are in current use: metal amalgams, such as the saturated calomel electrode (SEC); redox couples, such as a quinhydrone or ferri-ferrocyanide electrode; and metal/metal halide electrodes, such as the silver-silver chloride reference electrode. In the present invention, the reference electrode will generally be a silver/silver chloride button.

The subject of this invention is illustrated by the following examples, which are not to be considered limiting in any way.

EXAMPLE 1

Preparation of the Hydrogen Ion Specific Compound 2-octadecyloxy-5-carbethoxyphenylhydrazone mesoxalonitrile The hydrogen ion specific compound 2-octadecyloxy-5-carbethoxyphenylhydrazone mesoxalonitrile is prepared in the following manner. First, ethyl-4-octadecyloxy-3-nitrobenzoate is prepared according to the general procedure described in *Organic Synthesis*, Coll. vol. 3, pp 140–141.

The following mixture is refluxed for 72 hours in a 1-liter-3-neck flask fitted with a mechanical stirrer:
- 25 g (0.12 moles) of ethyl-4-hydroxy-3-nitrobenzoate Lancaster Synthesis, Windham, N.H. catalogue #6451
- 41 g (0.12 moles) of 96% 1-bromooctadecane Aldrich Chemical Co., Milwaukee, Wis. catalogue #19,949-4
- 16.4 g of anhydrous potassium carbonate 500 ml. of dry acetone At the end of the reflux period, the reaction mixture is cooled to room temperature (i.e., about 20°–27° C.) and filtered to remove salts. The filtrate is evaporated using a Buchi-Brinkman rotary evaporator. The residue is dissolved in 500 ml of toluene and washed in turn four (4) times with 400 ml of 5% aqueous sodium hydrogen carbonate and then one (1) time with 400 ml of saturated aqueous sodium chloride. The toluene layer is dried over anhydrous sodium sulfate and evaporated to dryness; this produces an oil which crystallizes on standing. The solid is recrystallized from hexane with charcoal clarification; the yield is 36g (66% yield) of ethyl-4-octadecyloxy-3-nitrobenzoate (m.p. 48°–56°).

The nitrocompound is reduced to the amino derivative by catalytic hydrogenation. To 200 ml of hexane is added 10 g of the above nitro compound along with 0.5 g 10% palladium on carbon. The mixture is placed on a Parr hydrogenator, heated to 40° C. under 60 psig of hydrogen and shaken in the machine for 18 hours. The reaction mixture is filtered through Celite filter aid medium (usually diatomaceous earth (Manville)) while hot (e.g., about 50° C.), and the solution is treated with HCl gas to precipitate the hydrochloride salt of the amine in nearly quantitative yield (m.p. 141°–145°).

The hydrochloride salt of ethyl-4-octadecyloxy3-aminobenzoate is converted to the mesoxalonitrile derivative according to a modification of the procedure of Brown et al. (U.S. Pat. No. 3,743,588). 8.5 g (0.018 moles) of the above hydrochloride salt is dissolved in 1 liter of dimethyl formamide (DMF) with warming and brought to a temperature of about 0°. 3 ml of concentrated HCl is added to the cold solution, followed by 1.3g of sodium nitrite dissolved in 500 ml of DMF. The reaction mixture is stirred magnetically for 1 hour. 1.15 ml of prewarmed malononitrile is then added and the mixture is stirred magnetically for about 10 minutes. Triethylamine is added in sufficient quantity to produce a strongly basic solution (e.g., pH greater than 9). The mixture is allowed to warm to room temperature and stirred for 18 hrs. The reaction mixture is acidified (to a pH of about 2.3) with concentrated HCl, and a precipitate results. The precipitate is filtered, washed with water and recrystallized from methanol. The result is about 7.0 g, (76%) of 2-octadecyloxy-5-carbethoxyphenylhydrazone mesoxalonitrile (m.p. 76°–77°). The other derivatives shown in Table 1 were prepared in a similar manner.

TABLE 1

| Membrane | R1 | R2 | R3 | Ionophore % (by weight) | Plasticizer % (by weight) | PVC % (by weight) | Slope pH 4–9 mv |
|---|---|---|---|---|---|---|---|
| 1 | $OC_{18}H_{37}$ | COOEt | H | 4.5 | 68.2 | 27.3 | 51 |
| 2 | $OC_{18}H_{37}$ | H | F | 2.3 | 69.8 | 27.9 | 50 |
| 3 | $OC_{18}H_{37}$ | $CF_3$ | H | 2.3 | 69.8 | 27.9 | 43 |
| 4 | $CF_3$ | H | $OC_{18}H_{37}$ | 2.3 | 69.8 | 27.9 | 19 |

EXAMPLE 2

Solvent Casting of a PVC Membrane and Incorporation Into an Ion-Selective Electrode 1.5 ml of 2-nitrophenyloctylether (Fluka Chemical Corp., Hauppauge, N.Y., cat #73732) and 0.10 g of the hydrogen ionophore (such as that prepared according to the method illustrated in Example 1) are dissolved in 10 ml of tetrahydrofuran. To this solution is added 0.6 g of powdered polyvinyl chloride of very high molecular weight and of density of 1.385 g/cc (Aldrich Chemical Co., Milwaukee, Wis., cat #18,261-3). The mixture is shaken (e.g., by vortexing) until the PVC is dissolved. The PVC solution is poured onto a ¼" thick sheet of stress-relieved polypropylene and allowed to remain under conditions which result in the evaporation of the tetrahydrofuran. For example, evaporation can occur at room temperature under a fume hood so that the tetrahydrofuran is removed as it evaporates. The product formed is a plastic membrane in which the ion-specific compound is incorporated. Disks are cut from the membrane using a #7 cork borer (id 0.5 in) and mounted in an Orion electrode body (Orion Research Inc., Cambridge, Mass., cat #950015). The internal reference electrode is a silver/silver chloride reference electrode and the internal filling solution is pH 7.4 phosphate buffered saline (SIGMA Chemical Co., St. Louis, Mo., cat #1000-3).

Assessment of the pH-sensing capability of the electrodes was carried out. All measurements were made versus a double junction Ag/AgCl reference electrode (Corning, cat #476067) in 250 ml beakers with magnetic stirring. For comparison a combination pH/reference electrode was dipped into the test solution to record pH changes, such that mv changes in the membranes can be related to pH changes measured with the glass electrode. The membrane of the present invention exhibited good mechanical strength, as indicated by the fact that it did not tear or break when stretched. It also exhibited good analytical performance, yielding slope values of 55–58 mv per decade over the pH range of 6 to 8 with performance decreasing somewhat on either side of this range. For a monovalent ion, the theoretical slope is ±59.1 mv at 25° C. In addition, the response time or the time to reach equilibrium was less than one minute and the electrodes required no preconditioning.

The properties of the above membrane were compared to those of a membrane prepared in an identical manner except that the hydrogen ion selective component was the previously described 3-chloro-4-octadecyloxyphenylhydrazone mesoxalonitrile. In contrast to the previous membrane, the membrane prepared from the chlorinated mesoxalonitrile gave diminished performance; slope values were 40 mv or less over the same pH range, indicating a loss in sensitivity.

The performance of the various hydrogen ionophores is summarized in Table 1. The results show that the three derivatives with the 18 carbon lipophilic chain ortho to the ionophoric site outperformed the derivative in which the lipophilic chain was para. This suggests that perhaps the lipophilic chain adjacent to the site of hydrogen ion exchange enhances the response towards hydrogen ions. The lipophilic chain could form a lipophilic pocket around the active site, thereby increasing the selectivity towards hydrogen ions.

EXAMPLE 3

Preparation of an Enzyme Electrode for the Measurement of Urea

A sensor as shown in FIG. 6 is used for the determination of urea. A urea-selective sensor is made by incorporating a second membrane containing the enzyme urease in the ion-selective electrodes of the sensor, which can be either a pH or an ammonium ion-($NH^+_4$) membrane. Urease-containing membrane are present in electrodes a, b and c shown in FIG. 4f. The two membranes are separated by a third membrane (e.g., membrane 52 of FIG. 6).

The sample to be tested (e.g., blood, plasma), a reference and a calibrant sample are added at the electrodes as shown in FIG. 4e.

A and B are wicks made of porous material and have been made conductive by the addition of a wetting agent. a, b and c are ammonium ion-selective electrodes. Two different known levels of urea, reference and calibrant are added at a and b, which have urease. Patient sample is added at c, which also has urease.

Reactions catalyzed by urease occur at b and c. This allows the comparison of the patient sample with two calibrant samples, thus allowing for the calibration of the test card.

The following reactions occur where urease is present:

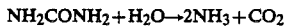

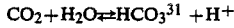

As a result, an ammonium selective membrane can be used to detect the change in ammonium ion ($NH_4^+$) concentration or a pH selective membrane can be used to detect the increase in pH which occurs because of the production of $OH^-$.

A urease containing membrane is prepared as follows: A 5 mg/ml urease (300 units/mg New England Enzyme Center, Boston, Mass.) solution is prepared in pH 7.4 phosphate buffered saline (Sigma Chemical Co., Cat. #1000–3): other buffers found to be useful are 10 mmol/L sodium Hepes in 0.1M NaCl (pH 7.4) and 10 mmol/L $NaH_2PO_4$ 10 mmol/L tris base in 0.1M NaCl (Ph 7.4). A 47 mm diameter disk of 12 micron pore size nitrocellulose membrane (Schleicher & Schuell, Inc., Keene, N.H., 03421 Grade AE 100) is soaked in 700 μl of the enzyme solution for 5 minutes at room temperature. The membrane is removed from the solution and the excess fluid scrapped off with a stirring rod. The membrane is placed on a hydrophobic surface (e.g., a sheet of polypropylene) and air dried at room temperature for 30 minutes. The membrane is stored in a closed container at 4° C. Disks are cut from the membrane and placed in the electrodes at a, b and c; see FIG. 4f. Sample solution (25 micro liters) is placed in c calibrating solutions can be placed in a and b. The urease in a, b and c acts on the urea in the calibrants and sample, liberating both ammonia and carbon dioxide ($CO_2$) The increase in pH or ammonia is measured.

For example, a pH 7.5 buffer was prepared containing 40 mmol/L $NaH_2PO_4$, 40 mmol/L tris base and 100 mmol/L NaCl. Buffer solutions containing 5 mmol/L urea and 10 mmol/L urea were prepared. After approximately one minute a 25 mv difference was observed when the 5 mmol/L urea solution was placed in a and c and buffer containing no urea was placed in b. A 50 mv difference was observed with the 10 mmol/L solution of urea. No difference in emf was observed in the absence of urea.

Similar behavior was observed when the pH membrane was replaced with an ammonium selective nonactin membrane.

EXAMPLE 4

Preparation of an Enzyme Electrode for the Measurement of Glucose

Referring to FIG. 4e, cells a, b and c each contain a membrane with immobilized glucose oxidase and catalase.

The following reactions occur where glucose oxidase (GOD) and catalase are present:

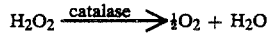

The purpose of the catalase is to recycle the oxygen consumed in the oxidation of glucose, thereby extending the linear range within which glucose may be measured. The glucose oxidase/catalase membrane was prepared as follows: The previously described nitro cellulose membrane was soaked in 700 micro liters of a solution consisting of 5 mg/ml glucose oxidase (300 units/mg, Boehringer Mannhein) and 1 mg/ml catalase (40,000 units/mg Sigma Cat. #C-100) in pH 7.4 phosphate buffered saline. The membrane was dried as in example 3. Enzyme disks were placed in a, b and c. The concentration of glucose in the sample was found to be proportional to the potential difference developed between b and c.

Another method for the determination of glucose uses the hexokinase/ATP as the enzyme system. Referring to FIG. 4e, cells 1, b and c each contain a membrane with immobilized hexokinase, ATP and a magnesium salt such as the chloride, acetate or sulfate.

The following reactions occur where hexokinase, ATP and magnesium ion are present:

The hexokinase/ATP membrane was prepared as follows: The previously described nitrocellulose membrane was soaked in 1.0 ml of a solution consisting of 10 g/L magnesium acetate, 50 mg/ml ATP, and 10 mg/ml hexokinase in a buffer consisting of 10% glycerol, 0.25% Triton X-100 and 0.005M triethalnolamine pH 7.8. The concentration of glucose in the sampel was found to be proportional to the potential difference developed between b and c.

EXAMPLE 5

Preparation of an Enzyme Electrode for the Measurement of Triglycerides

Referring to FIG. 4j, membranes containing enzyme, in this case lipase, are placed in cells a, b and c. The following reaction occurs where lipase is present:

As in the previous examples the membranes were prepared by soaking a nitrocellulose membrane in a 5 mg/ml. buffered solution of lipase (Sigma Chemical Co., Cat. #L4384). The decrease in pH which occurs upon addition of a sample containing triglycerides is detected with the pH electrode.

EXAMPLE 6

Preparation of an Enzyme Electrode for the Measurement of Uric Acid

As in the previous examples and referring to FIG. 4e, an electrode specific for uric acid is prepared by soaking a nitrocellulose membrane in a solution of uricase (50 units/ml Sigma Chemical Co., Cat. #U1878) plus catalase (1 mg/ml 40,000 units/mg Sigma Chemical Co., Cat. #C-100). The enzyme membrane is placed in cells a, b and c.

The following reactions occur where uricase and catalase are present: uric acid $+O_2+H_2O$ uricase Allantoin $+CO_2 +H_2O_2$

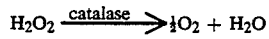

The $CO_2$ produced in the reaction causes a decrease in pH which is detected with the pH electrode.

EXAMPLE 7

Preparation of an Immunosensor for the Measurement of Theophylline

Figure 4L:
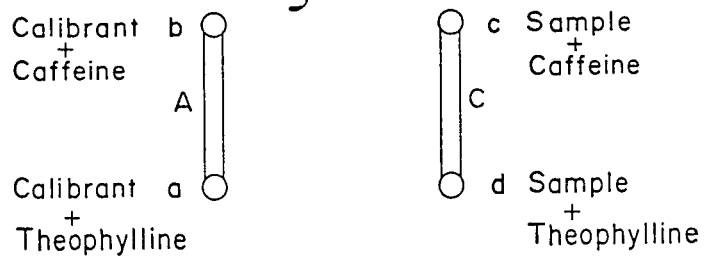
Figure 4M:
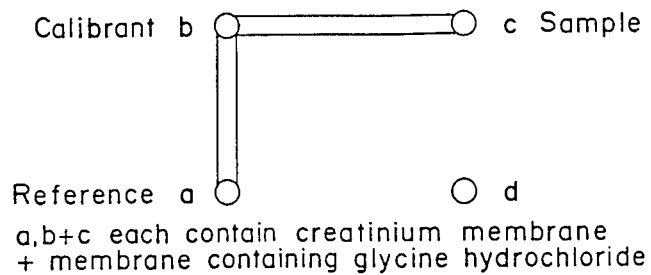

In the present case, the measurement of theophylline is based on differences in immunochemical reactivity between theophylline and caffeine. Caffeine differs from theophylline by a methyl group. Theophylline and caffeine have been coupled to a crown ether moiety and each conjugate has been incorporated into a PVC membrane. The theophylline membrane forms one half-cell while the caffeine membrane forms the other half-cell. The caffeine membrane serves as a reference electrode and separately, each membrane exhibits a response to potassium ion. However, when each membrane is incorporated into a concentration cell and the same solution containing potassium ion is placed in each half-cell, the emf developed between the two half-cells is very close to zero millivolts. Although the theophylline and caffeine conjugates exhibit identical behavior in the electrochemical sense, they differ greatly in their immunochemical reactivity towards theophylline antibody. This difference in immunochemical reactivity and identical ionophoric electrochemical reactivity, form the basis for a competitive binding differential potentiometric assay for theophylline. This method does not require constant ionic strength nor constant potassium ion activity (as in the Rechnitz approach). A major advantage of the present method resides in the fact that undiluted and undialyzed serum samples may be used. The arrangement of the sensor can be as represented in FIG. 4l.

The sensor consists of theophylline crown ether conjugate membranes in cells a and d and caffeine crown ether conjugate membranes in cells b and c, separated by porous junctions A and C. The sample containing theophylline is added to c and d while a calibrant is added to a and b. The competitive binding aspects require the presence of theophylline antibody with a low cross reactivity towards caffeine. The antibody may be added to the sample and calibrant before analysis in the sensor or the antibody may be contained within the sensor cells such that competitive binding occurs within the sensor. The competition for antibody site is set up between theophylline immobilized in the membrane and theophylline in the sample:

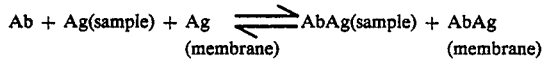

As theophylline antibody binds to the theophylline immobilized in the membranes (a and c) a change in potential develops, the magnitude of which is inversely proportional to the concentration of theophylline in the sample. So as the theophylline concentration in the sample increases, less antibody is available to bind to the membrane, and therefore, less of an emf is developed. For a typical assay, potential changes due to antibody binding are normally on the order of a few millivolts. Another advantage in using the differential approach with a theophylline membrane, versus or in combination with a caffeine "reference" membrane, is that the common mode or initial starting potential is near zero millivolts and the signal to be measured is on the order of millivolts. The low common mode potential allows for greater senstivity in the measurement of the signal voltage and therefore a more accurate and precise signal measurement is possible when the background or common mode voltage is less than the signal voltage. As previously discussed, the potential difference between the theophylline and caffeine half-cells is nearly zero when treated with the same potassium ion-containing sample. However, when either half-cell is replaced with a reference electrode such as an SCE or a silver-silver chloride reference electrode, the potential difference with the same potassium ion solution increases to as much as 50 mv or more.

The synthesis of the conjugates and the method of preparation of the membranes is described below:

Reaction Scheme for the Preparation of Theophylline Benzo-15-Crown-5-Conjugate
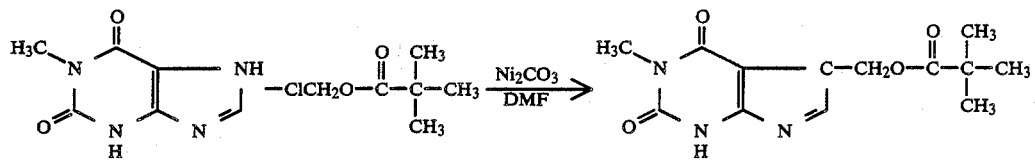
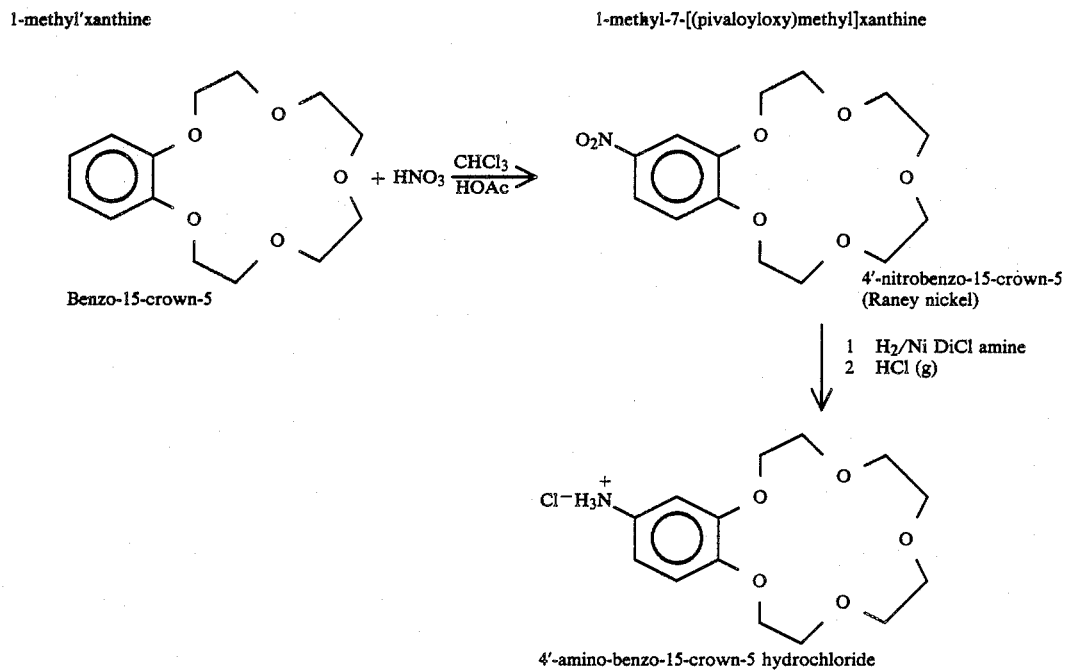
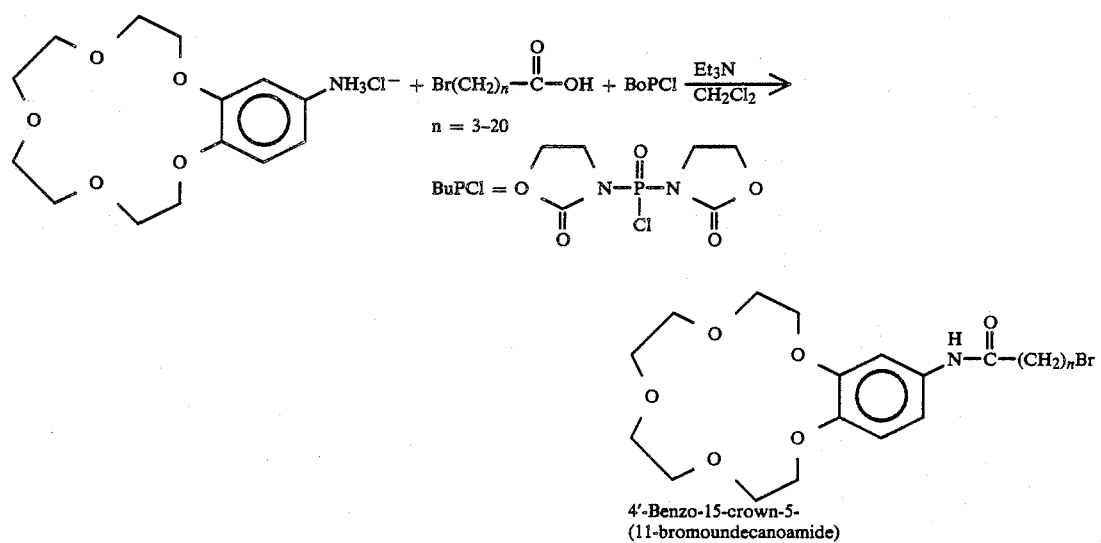
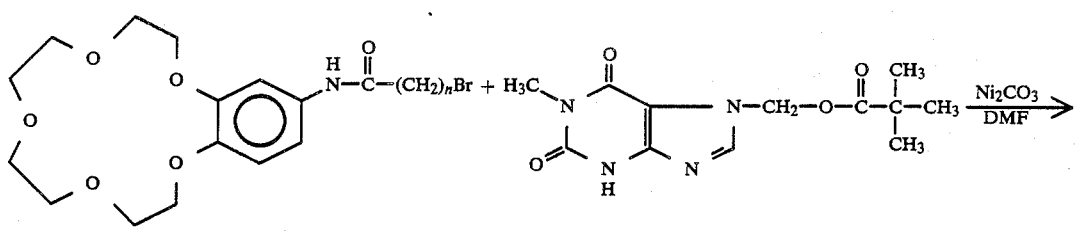

Reaction Scheme for the Preparation of Theophylline Benzo-15-Crown-5-Conjugate

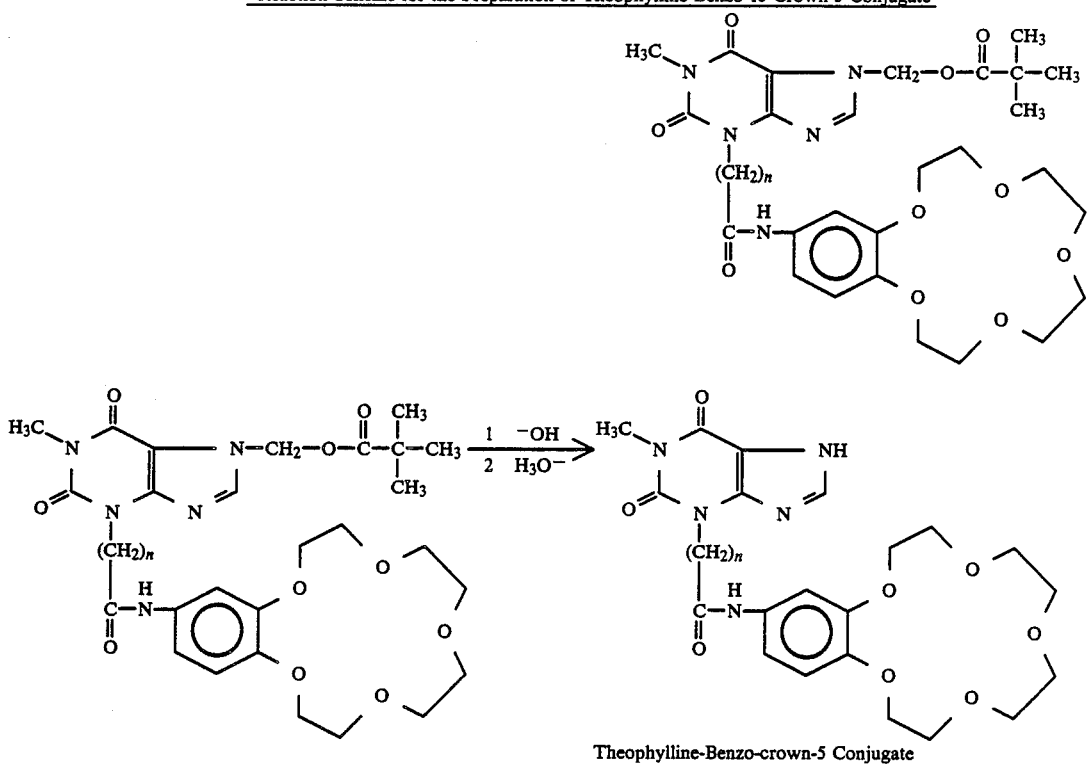

Theophylline-Benzo-crown-5 Conjugate

The first step in the synthesis involves blocking the 7 position in 1-methyl xanthine. The procedure of Hu, Singh and Ullman, *J. Am. Chem. Soc.*, 45: 1711–1713 (1980) was followed. To 700 ml of dry DMF in a 1-liter conical flask was added 3.2 g (18.9 mmoles) of 98% 1-methylxanthine (Aldrich Chemical Co., cat. #28,098-4), the mixture was stirred magnetically and warmed until dissolution occurred and then cooled to room temperature. To the stirred solution was added 2.0 g (18.9 mmoles) of anhydrous sodium carbonate followed by the dropwise addition, over a period of 1 hour, of 3.0 g (19.3 mmoles) of 97% chloromethyl pivalate (Aldrich Chemical Co., cat. #14,118-6) dissolved in 50 ml of DMF. The reaction mixture was stirred overnight at room temperature. The reaction mixture was evaporated to dryness and the residue treated with 50 ml of methylene chloride. The insoluble material was collected by filtration and washed with 1N HCl to give 1.24 g of 1-methylxanthine. The methylene chloride solution was evaporated to dryness to yield a mixture of mono- and bis- protected xanthine. The mono-protected 1-methyl-7-}pivaloyloxy)methyl1 xanthine was separated from the bis protected xanthine by crystallization from ethyl acetate. By this method there was obtained 1.5 g of the monoprotected xanthine (m.p. 204°–206°). The ethylacetate filtrate from the isolation of the mono-protected xanthine, containing the bis-protected xanthine, was evaporated to dryness and refluxed with 20 ml of 2N sodium hydroxide for 18 hours. The reaction mixture was cooled and acidified with concentrated HCl and extracted with chloroform. Evaporation of the aqueous layer yielded 0.5 g of 1-methylxanthine.

The second step in the synthesis is the preparation of 4′-amino-benzo-15-crown-5 hydrochloride. To a stirred solution of 30 g (6.11 mmoles) of benzo-15-crown-5 (Parish Chemical Co., Orem, Utah, cat. #1405) in 800 ml of 1:1 glacial acetic acid/chloroform was added dropwise, over a period of 1 hour, a solution of 15 ml concentrated nitric acid dissolved in 50 ml of glacial acetic acid. The reaction mixture was stirred for one hour and then evaporated to dryness on a rotary evaporator. The residue was treated with 500 ml of 5% aqueous sodium hydrogen carbonate and the mixture partitioned with 500 ml of chloroform. The chloroform layer was washed with saturated aqueous sodium chloride and dried over anhydrous sodium sulfate. Evaporation of the chloroform yielded 30 g (86%) of 4′-nitoben-zo-15-crown-5. The product was recrystallized from ethanol and 15 g (48 mmoles) dissolved in 250 ml of dioxane and catalytically reduced over Raney nickel (Aldrich Chem. Co., cat. #22,167-8) in a Paar hydrogenator at 50° C.

The reaction mixture was filtered and the filtrate evaporated to dryness and the residue dissloved in 200 ml of ethyl acetate. The solution was then treated with HCl gas to precipitate the hydrochloride salt of 4′-amino-benzo-15-crown-5. Yield 9.0 g (58%).

The third step in the synthesis is the preparation of 4′-benzo-15-crown-5-(11-bromoundecanoamide). To 10 g (37.7 mmoles) of 11-bromoundecanoic acid (Aldrich Chemical Co., cat. #B8,280.4) in 100 ml of $CH_2Cl_2$ in a 250 conical flask was added 5.5 ml of triethylamine. The mixture was cooled to 0° C. and 9.67 g of N,N-Bis[2-oxo-3-oxazolidinyl] phosphordiamidic chloride (BOPCL, Chemical Dynamics Corp., cat. #12-1370-00) was added. The mixture was stirred for 0.5 hours then 12.06 g (37.7 mmoles) of 4′-amino-benzo-15-crown hydrochloride was added along with 5.5 ml of triethylamine. To the reaction mixture was added dropwise another 5.5 ml of triethylamine in 50 ml of $CH_2Cl_2$ over a period of 1 hour. The reaction mixture was allowed to warm to room temperature for 18 hours. Water (50 ml)

was added and the mixture acidified with concentrated HCl. The CH$_2$Cl$_2$ layer was washed in turn 3 times with 200 ml saturated NaCl solution and 3 times with 200 ml 5% sodium hydrogen carbonate solution. The CH$_2$Cl$_2$ layer was dried over anydrous sodium sulfate and evaporated to dryness. The residue was crystallized from hexane/ethyl actetate to yield 8.8 g (44%) of 4'-benzo-15-crown-5-(11-bromoundecanoamide), m.p. 101°-103°, analysis calaculated for C$_{25}$H$_{40}$BrNO$_6$, C:56.60; H:7.60, Br:15.06; N:2.62. Found: C:56.41; H:7.46; Br.:14.89; N:2.60.

In the fourth step, the crown ether was coupled to the protected 1-methylxanthine. To 50 ml of DMF in a 125 ml conical flask was added 1.0 g (3.57 mmole) of 1-methyl-7-[(pivaloyloxy)methy] xanthine. The mixture was warmed (e.g., to about 80° C. with stirring) until dissolution. The solution was cooled to room temperature and 0.76 g (7.1 mmole) of anhydrous sodium carbonate was added followed by the addition of 1.90 g (3.57 mmole) of the crown ether amide. The reaction mixture was stirred under nitrogen for 3 days. The DMF was removed by rotary evaporation and 100 ml of water was added and the mixture extracted 3 times with 50 ml of chloroform. The combined chloroform extracts were washed 1 time with 100 ml of saturated aqueous sodium chloride and dried over anhydrous sodium sulfate. Evaporation of the chloroform yielded a pale brown oil.

The fifth step is the removal of the protecting group with aqueous base. To the above oil in a 250 ml round bottom flask was added 75 ml of 0.2M NaOH and 25 ml of methyl alcohol. The mixture was refluxed for 1 hour and cooled to room temperature. The solution was acidified with concentrated HCl with cooling in an ice/acetone bath. The precipitated product was recrystallized from ethyl alcoholwater to yield 1.2 g (55%) of an off-white crystalline solid, m.p. 166°-170°. The material was homogenous by hplc analysis. Analysis calculated for C$_{31}$H$_{45}$N$_5$O$_8$: C:60.47; H:7.37; N:11.37. Found: C:60.25; H:7.23; N:11.09. The benzo-12-crown-4 derivative was prepared by a similar method.

Preparation of Caffeine-Benzo-15-Crown-5 Conjugate

The caffeine conjugate was prepared according to step 4 in the reaction scheme except that the protected 1-methyl xanthine was replaced with 1,7-dimethyl xanthine.

To 50 ml of DMF in a 125 ml conical flask was added 1.0 g (5.56 mmole) of 1,7-Dimethylxanthine. The mixture was warmed with stirring until dissolution occurred. The solution was cooled to room temperature and 0.59 g of anydrous sodium carbonate was added followed by the addition of 2.95 g (5.56 mmole) of the previously described crown ether amide and the reaction mixture stirred for 3 days. The DMF was removed by rotary evaporation and 100 ml of water was added and the mixture extracted 3 times with 50 ml of chloroform. The combined extracts were washed 1 time with 100 ml of saturated aqueous sodium chloride and dried over anhydrous sodium sulfate. Evaporation of the chloroform yielded a brown oil which was crystallized from hexane-ethyl acetate to yield 1.0 g (29%) of product. The product was recrystallized from ethylacetate/hexane with charcoal clarification and found to be homogenous by hplc. m.p. 130°-133°. Analysis calculated for C$_{32}$H$_{47}$N$_5$O$_8$: C:61.03; H:7.52; N:11.12. Found: C:60.78; H:7.53; N:10.97. The benzo-12-crown-4 derivative was prepared by a similar method.

Preparation of A Drug Specific Electrode for The Measurement of Theophylline

Theophylline Membrane

The components for the theophylline membrane consisted of: 0.005 g theophylline-crown ether conjugate, 0.02 g potassium tetra(p-chlorophenyl) borate, 0.5 ml bis(2-ethylhexyl) sebacate, 0.3 g high molecular weight PVC and 5 ml THF. The membrane can be formed by either solvent casting or dip coating as previously described.

Caffeine Membrane

The components for the caffeine membrane consisted of: 0.005 g caffeine-crown ether conjugate, 0.02 g potassium tetra(p-chlorophenyl) borate, 0.5 ml bis-(2-ethylhexyl) sebacate, 0.3 g high molecular weight PVC and 5 ml THF. The membrane can be formed by either solvent casting or dip coating as previously described.

Differential Measurement Technique

One membrane each of theophylline and caffeine was mounted in an Orion 95 electrode body. The internal filling solution consisted of pH 7.4 phosphate buffered saline and the reference electrodes were silver-silver chloride wires. The two electrodes were fitted into a rubber stopper and immersed into 5.0 ml of pH 7.4 phosphate buffered saline. The solution was magnetically stirred. The emf measured between the two electrodes was 0.23 mv. To test the response to potassium ion, 100 μl of 0.2 molar KCL was pipetted into the stirred buffer solution. A transient response was observed as evidenced by a sharp peak (0.3 mv) on the output of a strip chart recorder. The potential difference returned to the base-line value within 30 to 60 s. The transient response to potassium is probably due to a local concentration of potassium ion near the membrane surface which disappears as the solution is mixed.

To test the response to protein, 100 μl of a standard protein solution (Sigma Chemical Co., St. Louis, Mo., Cat. #540-10) consisting of 3.5 /dl albumin and 3.0 /dl globulin was added to the solution. The standard protein solution had no effect on the electrode potential.

When, however, 100 μl of theophylline antibody (Immunotech Corp., Allston, Mass., Cat. #651 or Research Plus, Bayonne, N.J., Cat. #01-9603-09) was added the potential difference between the two electrodes shifted by 0.85 mv over a period of about 20-30 min.

A sensor of this type can be used in a competitive binding assay. The antibody which remains unbound in the sample is measured and provides an indirect measure of antigen present in the sample. The more antibody bound by the antigen in the sample, the lower the resulting electrical signal because less antibody will be available for binding to the antigen immobilized in the sensor membrane; that is, antigen concentration will be inversely related to the magnitude of the signal.

EXAMPLE 8

Preparation of an Ion Selective Electrode for the Measurement of Creatinine

Creatinine is an important indicator of renal function and its measurement in serum is a routinely performed blood test. Presently, in the clinical laboratory there are two ways of determining creatinine. The more widely used method is the Jaffe reaction, which is based on the production of a red colored complex between creatinine and picrate in alkaline solution. This method gives erroneous results in the presence of certain metabolites and drugs. The second method utilizes an enzyme. Although enzymic methods are highly specific, the expense and the time required to carry out a test restrict their routine use in clinical laboratories.

Most recently a creatininium ion selective electrode has been descrbed. E. P. Diamondis and T. P. Hadjiiannou, Anal. Lett., 13, 1317–1332 (1980). The creatinium ion exchanger was prepared by mixing equimolar aqueous solutions of creatinine and sodium tetraphenylboron followed by the addition of a hydrochloric acid solution which results in precipitation of the complex salt creatininium tetraphenylboron. The salt was extracted into 2-nitrotoluene and this solution of the complex salt used as a liquid ion exchanger in an Orion 92 (Orion Research, Cambridge, Mass.) electrode equipped with Teflon membranes. In this type of ion selective electrode the ion exchange material is in liquid form contained in a reservoir and continuously leaches through the membrane into the sample solution and therefore must be periodically replenished. The electrode was conditioned by soaking in 0.01 mol/L creatininium chloride for 24 hours before use. The response of the creatininium electrode at pH 3 was linear in the $10^{-3}$ to $10^{-1}$ mol/L range with a slope of 57 mv at 20° C. The slope decreased to 37 mv in the $10^{-4}$ to $10^{-3}$ mol/l range.

The present invention makes use of a plastic membrane in which the ion exchange material is immobilized. When creatininium tetraphenyl boron was incorporated into a PVC membrane using 2-nitrotoluene as a plasticizer a slope of 44 mv was obtained between $10^{-3}$ and $10^{-1}$ mol/L creatininium chloride and decreased to 14 mv in the $10^{-4}$ to $10^{-3}$ mol/L range. The clinically important range for creatinine is $10^{-4}$ to $10^{-3}$ mol/L. The use of other nitrated plasticizers such as 2-nitro-p-cymene and 2-nitrophenyloctyl ether did not improve the sensitivity in the $10^{-4}$ to $10^{-3}$ mol/L range.

A significantly improved response in the $10^{-4}$ to $10^{-3}$ mol/L range was obtained when a substituted tetraphenylboron salt was used having the general formula:

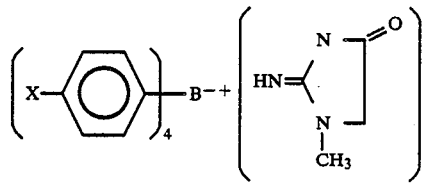

where x=Cl, Br, F, CF$_3$ In one embodiment, a membrane was prepared consisting of 0.02 g of creatininium tetra-(p-chlorphenyl) boron, 1.5 ml of 2-nitrophenyloctyl ether, 0.3 g of very high molecular weight PVC, and 5 ml of THF. The membrane was prepared either by solvent casting or by dip coating as previously described. The membrane yielded a slope of 55 mv between $10^{-3}$ ml/L and $10^{-1}$ mol/L creatininium chloride and 40 mv in the $10^{-4}$ to $10^{-3}$ mol/L range and did not require any preconditioning. The substituted tetraphenyl boron salts exhibited much higher sensitivity in the clinical range of concentration than the unsubstituted tetraphenyl boron salt. The performance of the various substituted tetraphenyl boron salts is summarized in Table 2.

The unexpected increase in sensitivity of the substituted tetraphenyl boron salts over the unsubstituted tetraphenyl boron may be attributed to an increase in lipophilicity and differences in the nature of the ionic exchange properties of the complexes formed with the substituted tetraphenyl boron salts. In practice, the pH of the solutions containing creatinine must be decreased to a pH of 3 or less by the addition of acid. This can be accomplished by dilution of the sample with an acid solution. However, in the case of a serum sample, significant dilution may adversely effect the sensitivity of the assay due to a decrease in the concentration of creatinine.

In the present case a different approach was taken. The pH of the sample containing creatinine was lowered by treating the sample with a support containing dried glycine hydrochloride. This was accomplished by dipping a membrane support such as nitrocellulose (Schleicher and Schull 12 micron, grade HE-100) into an aqueous solution of glycine hydrochloride (0.1 to 1.0 moles/L). A sandwich was formed such that the nitrocellulose membrane covered the surface of the creatininium tetra (p-chlorophenyl) boron PVC membrane. Referring to FIG. 4k, each cell a, b and c contains a creatininium PVC membrane and a nitrocellulose membrane containing glycine hydrochloride. The serum sample is added to c and reference and calibrant solutions are added to a and b, respectively. The glycine hydrochloride converts the creatinine to creatininium hydrochloride which is detected by the membrane.

The emf developed between a and b may be used to calibrate the sensor. The slope from a and b and the emf developed between b and c may then be used to determine the creatinine concentration in the sample.

Preparation of Creatininium Tetraphenyl Boron Salts

The creatininium tetraphenyl boron salts were prepared by mixing equimolar aqueous solutions of creatininium hydrochloride (Sigma Chemical Co., St. Louis, Mo., Cat. #C-6257) and the corresponding sodium salt of the substituted tetraphenyl boron. The precipitated salts were collected by filtration, washed with water and dried. The sodium salts of the substituted tetraphenyl boron derivatives were prepared by the method of Cassoretto, McLafferty and Moore, Anal. Chem. Acta, 32:376–380 (1965) and involved the following steps:

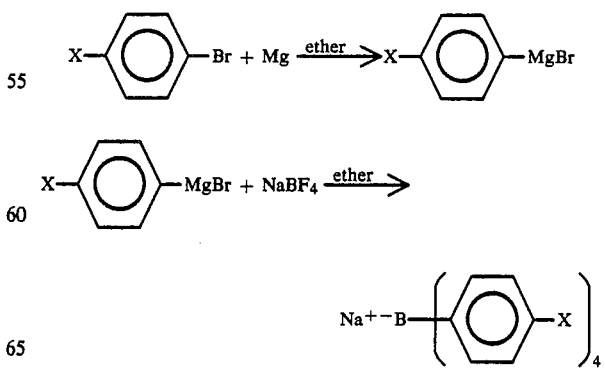

X = F,Cl,CF$_3$

TABLE 2

Response of Creatininium Tetraphenyl Boron Salts to Creatininium Hydrochloride.

$$\left( X-\!\!\left\langle\bigcirc\right\rangle-\!\right)_{\!4}\!\!B^{-}+\left( HN\!=\!\!\begin{array}{c}\phantom{a}\\[-2pt]\end{array}\!\!\!\begin{array}{c}N\!-\!\!\!\diagdown\!\!O\\[-2pt] \phantom{a}\\[-2pt] N\!-\!\!\!\diagup\\[-2pt] |\\[-2pt] CH_3 \end{array}\right)$$

| X | $10^{-1}$ to $10^{-3}$ mol/L Slope (mv) | $10^{-3}$ to $10^{-4}$ mol/L Slope (mv) |
|---|---|---|
| H | 50 | 10 |
| F | 45 | 26 |
| Cl | 55 | 36 |
| CF$_3$ | 57 | 40 |

All mv readings shown in Table 2 are versus a double junction silver-silver chloride reference electrode. The creatininium solutions used were prepared with 0.05M glycine-glycine hydrochloride buffer pH 3.0 containing 150 mM sodium chloride and 6 mM potassium chloride.

EXAMPLE 9

Preparation of an Ion Selective Electrode for the Measurement of Sodium

A membrane selective to sodium ions was prepared using the following proportions of components: 0.2 g methylated monensin, 0.04 g sodium tetra-(p-chlorophenyl) borate, 2.0 ml 2-nitrophenyloctyl ether, 1.2 g high molecular weight PVC, 12 ml tetrahydrofuran (THF) and 5 ml 4-methyl-2-pentanone. The membrane can be formed by either solvent casting or dip coating as previously described.

The membrane was incorporated into the previously described electrode housing and tested using aqueous sodium ion containing solutions. The sensor yielded a slope of 57–60 mv per decade at 25°.

Preparation of Methylated Monensin

To 250 ml of 1,4-dioxane in a 500 ml round bottom flask was added 5.0 g of sodium monensin (Sigma Chemical Co., St. Louis, Mo., Cat. #M2513) along with 20 ml of iodomethane. The mixture was gently refluxed for 18 hours and then evaporated to dryness on a rotary evaporator. The residue was dissolved in 200 ml of methylene chloride and washed in turn 2 times with 500 ml saturated aqueous sodium chloride, 2 times with 200 ml 5% aqueous sodium hydrogen carbonate and one time with 200 ml of saturated aqueous sodium chloride. The methylene chloride solution was dried over anhydrous sodium sulfate and evaporated to dryness. The residue was treated with 50 ml of hexane with warming in a 50° water bath. The hexane solution was cooled in a freezer for 1-2 hours followed by filtration to remove precipitated salts. The hexane solution was evaporated to dryness to yield 2.5–4.0 g of a light tan oil. The oil was used to prepare the sodium selective membrane.

EXAMPLE 10

Preparation of an Ion Selective Electrode for the Measurement of Potassium

A membrane selective to potassium ions was prepared using the following proportions of components: 0.2 g valinomycin, 0.04 g potassium tetraphenyl borate, 2.0 ml 2-nitrophenyloctyl ether, 1.2 g high molecular weight PVC, 10 ml THF and 5 ml 4-methyl-2-pentanone. The membrane can be formed by either solvent casting or dip coating as previously described.

EXAMPLE 11

Preparation of an Ion Selective Electrode for the Measurement of Chloride

A membrane selective to chloride ions was prepared using the following proportions of components: 1.0 ml Aliquat 336 (Aldrich Chemical Co., Milwaukee, Wis., Cat. #20,561-3), 2.0 ml tris (2-butoxyethyl) phosphate (Aldrich Chemical Co., Milwaukee, Wis., Cat. #13,059-1), 1.2 g very high molecular weight PVC (Aldrich Chemical Co., Milwaukee, Wis., Cat. #18,261-3), 12 ml THF and 5 ml 4-methyl-2-pentanone. The membrane can be formed by either solvent casting or dip coating as previously described.

Industrial Utility

This invention has industrial utility in the determination of the ion content or concentration of other constituents of samples, in particular biological fluids such as blood, serum, plasma, urine, saliva and cerebrospinal fluid. It is particularly useful for the rapid determination of the ion activity of a biological sample, as well as the concentration of other sample components, such as glucose, urea, triglycerides, creatinine, uric acid, lipase, other enzymes and drugs. It is well suited for use in a clinical or research context because there is no need for preconditioning of the ion-selective membrane and because it provides results quickly. In addition, the invention can be used for the similar determination in other samples such as beverages, meats, canned and processed foods, fruit extracts, etc.

Equivalents

Those skilled in the art will recognize, or be able to ascertain using no more than routine experimentation, many equivalents to the specific components and materials described specifically herein. Such equivalents are intended to be encompassed in the scope of the following claims.

We claim:

1. A sensor for the potentiometric determination of the activity of an ion or other concentration of a component in a sample, the ion being selected from the group consisting of hydrogen ions, potassium ions, sodium ions, chloride ions, ammonium ions, carbonate ions, bicarbonate ions, and calcium ions, the sensor comprising:
   a. a frame having an upper section and a lower section, each section having at least two openings therethrough and grooves in the mating surfaces thereof between the openings, the upper section and the lower section mating in such a relationship that the holes in the two sections are aligned and the grooves in the mating surfaces are aligned to form internal channels between the openings;
   b. ion selective electrodes in the openings, each electrode being comprised of:
      1. an ion selective membrane which is comprised of an ionophore selective for the ion whose activity is to be determined; a thermoplastic resin or a plastic; and a plasticizer;
      2. a reference electrode; and 3. an internal reference material having a known concentration of the ion whose activity is to be determined;

c. retainer means for securing the ion selective membranes in the openings; and d. porous material in the spaces between the openings in the sensor frame, the porous material, when conductive, providing ionic flow between the ion selective electrodes in the openings.

2. The sensor of claim 1 in which the ion selective membranes are from about 1 mil to about 15 mil in thickness and are comprised of from about 1 to about 10 percent by weight of an ionophore selective for the ion whose activity is to be determined; from about 10 about 30 percent by weight of a thermoplastic resin or a plastic; and from about 50 to about 80 percent by weight of a plasticizer.

3. A sensor of claim 1 in which the ion selective membranes are additionally comprised of a mesh material.

4. A sensor of claim 3 in which the mesh material is a nylon mesh material or a polyester mesh material.

5. A sensor of claim 1 in which the ion selective membrane is additioally comprised of; (a) an enzyme which catalyzes a reaction which produces a change in pH or a change in ammonium ion concentration of the sample or (b) a substance which is a substrate of an enzymatic reaction which products a change in pH or a change in ammonioum ion concentration of the sample, the enzyme or the substrate being immobilized on the membrane.

6. A sensor of claim 1 wherein there is:

a. a first ion-selective electrode, a second ion-selective electrode and a third ion-selective electrode, each having a silver/silver chloride reference electrode, said said first electrode and said second electrode containing a fixed concentration of the ion whose activity is to be determined; and b. a conductive, porous material between said first and said second electrodes and between said second and said third electrodes, one of said ion-selective electrodes comprising the same components as the electrode to which the sample is applied and another of said ion-selective electrodes serving as a reference electrode having a known concentration of the ion whose concentration in the sample is being determined.

7. A sensor of claim 6 wherein the ion whose activity is to be determined is hydrogen, the ionophore is selective for hydrogen ion and the internal reference material comprises a buffer solution of known pH.

8. A sensor of claim 6 wherein the ion whose activity is to be determined is potassium ion, the ionophore is selective for potassium ion and the internal reference material comprises potassium chloride of known potassium ion concentration.

9. A sensor of claim 6 wherein the ion whose activity is to be determined is sodium ion, the ionophore is selective for sodium ion and the internal reference material comprises sodium chloride of known sodium ion concentration.

10. A sensor of claim 6 wherein the ion whose activity is to be determined is chloride ion, the ionophore is selective for chloride ion and the internal reference material comprises sodium chloride of known chloride ion concentration.

11. A sensor for the potentiometric determination of the activity in a sample of an enzyme which catalyzes a reaction which results in a change in ionic activity of the sample or the concentration in a sample of a component which is a substrate for an enzymatic reaction which results in a change in ionic activity of the sample, the sensor comprising:

a. a frame having an upper section and a lower section, each section having at least two openings therethrough and grooves in the mating surfaces thereof between the openings, the upper section and the lower section mating in such a relationship that the holes in the two sections are aligned and the grooves in the mating surfaces are aligned to form internal channels between the openings;

b. ion selective-electrodes in the openings, each electrode being comprised of:

1. a layer having at least one enzyme which catalyzes a reaction which results in a change in ionic activity of the sample or at least one substrate of a reaction which results in a change in ionic activity of the sample immobilized thereon;

2. an ion selective membrane comprised of an ionophore selective for the ion the activity of which is changed in the sample; a thermoplastic resin or a plastic; and a plasticizer;

3. a reference electrode; and 4. an internal reference material having a known concentration of the ion whose activity in the sample changes as a result of the enzyme whose activity is being determined;

c. retainer means for securing the ion selective membranes in the openings; and d. porous membranes in the spaces between the openings in the sensor frame, the porous material, when conductive, providing ionic flow between the ion selective electrodes in the openings.

12. A sensor of claim 11 in which the enzyme immobilized on the layer is selected from the group consisting of urease, glucose oxidase, catalase, uricase, lipase; the substrate immobilized on the layer is selected from the group consisting of L-alanine, L-aspartate, starch, creatinine and creatine; and the ion selective membranes are from about 1 mil to about 15 mil thickness and are comprised of from about 1 to about 10 percent by weight of an ionophore, from about 10 to about 20 percent by weight of a thermoplastic resin or a plastic, and from about 50 to about 80 percent by weight of a plasticizer.

13. A sensor of claim 11 in which the ion selective membranes are additionally comprised of a mesh material.

14. A sensor of claim 13 in which the mesh material is a nylon mesh material or a polyester mesh material.

* * * * *